United States Patent
Fukuyama et al.

(10) Patent No.: US 7,820,838 B2
(45) Date of Patent: Oct. 26, 2010

(54) METHOD FOR TOTAL SYNTHESIS OF ECTEINASCIDINS AND INTERMEDIATE COMPOUNDS THEREOF

(75) Inventors: Tohru Fukuyama, Tokyo (JP); Toshiyuki Kan, Tokyo (JP)

(73) Assignee: Japan Science and Technology Agency, Saitama (JP)

( * ) Notice: Subject to any disclaimer, the term of this patent is extended or adjusted under 35 U.S.C. 154(b) by 6 days.

(21) Appl. No.: 12/178,939

(22) Filed: Jul. 24, 2008

(65) Prior Publication Data

US 2009/0036673 A1      Feb. 5, 2009

Related U.S. Application Data

(62) Division of application No. 10/498,367, filed as application No. PCT/JP02/09690 on Sep. 20, 2002, now Pat. No. 7,417,145.

(30) Foreign Application Priority Data

Jan. 29, 2002    (JP) .............................. 2002-019360

(51) Int. Cl.
*C07D 317/54*      (2006.01)
*C07D 405/06*      (2006.01)
*C07D 317/50*      (2006.01)
*C07D 413/04*      (2006.01)
*C07D 241/38*      (2006.01)

(52) U.S. Cl. ................. 549/437; 544/148; 544/338; 544/153; 544/343; 544/377; 544/344; 544/342; 549/213; 549/214

(58) Field of Classification Search ............ 544/214; 514/63; 549/214
See application file for complete search history.

(56) References Cited

OTHER PUBLICATIONS

Endo, "Total Synthesis of Ecteinascidin 743", J. Am. Chem. Soc. 2002, vol. 124, 6552-6554.*

Corey, "Enantioselective Total Synthesis of Ecteinascidin 743", J. Am. Chem. Soc. 1996, vol. 118, 9202-9203.*

Tohma, "Synthesis of Optically Active alpha-Arylglycines: Stereoselective Mannich-Type Reaction with a New Chiral Template", Synlett 2001, No. 7, 1179-1181.*

Endo, "Synthetic Study on Ecteinascidin 743 Starting From D-Glucose", Synlett 1999, No. 7, 1103-1105.*

Hinterding, "Synthesis and In Vitro Evaluation of the Ras Farnesyltransferase Inhibitor Pepticinnamin E", Angew. Chem. Int. Ed. 1998, 37, No. 9 1236-1239.*

* cited by examiner

*Primary Examiner*—James O Wilson
*Assistant Examiner*—Susanna Moore
(74) *Attorney, Agent, or Firm*—Hahn & Voight PLLC; Roger C. Hahn

(57) ABSTRACT

An intermediate compound for total synthesis of ecteinascidins comprising, a compound represented by general formula 2 having thioether group at C4 site, and the substituent $R_2$ of $N_{12}$ site is trichloroethoxycarbonyl (Troc) to which various substituents can be introduced by mild condition, further having 10 members ring structure which can be converted to a ring of other numbered members.

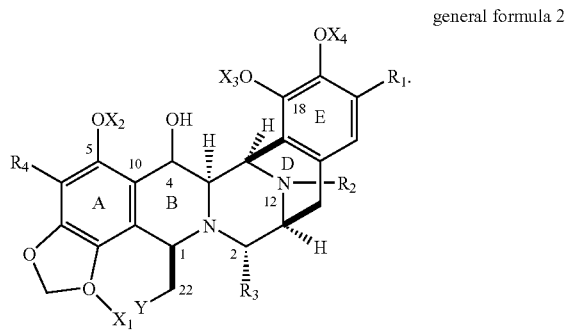

general formula 2

3 Claims, No Drawings

METHOD FOR TOTAL SYNTHESIS OF ECTEINASCIDINS AND INTERMEDIATE COMPOUNDS THEREOF

CROSS-REFERENCE

This application is a divisional of U.S. patent application Ser. No. 10/498,367, U.S. Pat. No. 7,417,145, filed Jun. 10, 2004, which is a §371 application of PCT/JP02/09690, filed on Sep. 20, 2002, which claims priority to JP 2002/19360, filed on Jan. 29, 2002.

FIELD OF THE INVENTION

The present invention relates to intermediate compounds useful for the total synthesis of ecteinascidin 743 (hereinafter shortened to Et 743) having high antineoplastic activity, the analogous structural compounds to Et 743 and the method for synthesis of Et 743.

BACKGROUND OF THE INVENTION

Ecteinascidins are a group of marine alkaloid having antineoplasticity which is isolated from the extracted products from the marine tunicate habitat of the Caribbean sea by a very small amount. Arming the ecteinascidins, Et 743 has a very strong antineoplastic activity, studies to put it into practical use as a carcinostatic agent are limited, and the phase II clinical tests are now being carried out in ten countries in Europe and America. It is known that Et 743 has an effect of depressing the proliferation of cancer cells by 10 to 100 times more potent than (IC50=0.1-1 nM) Toxol, Camptotesin, Adriamycin or Mitomycin which are currently used carcinostatic agents.

From the background mentioned above, various studies for synthesis were carried out; however, the complete synthesis was only reported by Prof. E. J. Corey of Harvard University in the U.S.A. (J. Am. Chem. Soc. 1996, 118, 9202-9203, reference document A).

In the process of the total synthesis disclosed in Document A (refer to page 9202), the main feature of the process is that Et 743 is synthesized from the analogous compound to the compound represented by general formula 1 of the present invention via intermediates 4 and 8. That is, according to said process, the $C_4$ site of ring B (regarding the location of rings, and the sites of atoms comprising the 6 membered ring, refer to general formula 1), which composes a 6 membered ring, is formed from the intermediate 4 at the first step. Since the atom $C_4$ composing the ring B of the 6-membered ring H, which lacks reactivity, is bonded, it becomes necessary to perform an oxidation reaction at the $C_4$ site on the B ring. This oxidation reaction is not effective and is carried out under harsh conditions; therefore production on an industrial scale is difficult, and also the yield is not good. Further, since the atom $N_{12}$ site of the synthesized intermediate is substituted by an alkyl group which lacks reactivity, in this case substituted by a methyl group, it is not suited to the synthesis of various compounds. Although total synthesis was reported, the supplying source of Et 743 still depends on the natural sample whose supply is very scarce. Therefore, the establishment of the method for Et 743 is desired and requires accomplishing an effective synthesizing process.

Since ET 743 is known as a medicine having high antineoplasticity, and phthalascidin induced from the intermediate product at the synthesis of Et 743 displays the same activity to ET 743, the establishment of an effective and mild method for synthesis of ET 743 and analogous compounds thereof is strongly desired.

Therefore, the subject of the present invention is to accomplish the effective method for total synthesis of Et 743, and further, to provide not only Et 743 but also analogous compounds.

To dissolve the subject, the present invention uses retrosynthetic analysis for easy synthesis. It will be possible to form a B ring by a ring forming reaction at the ortho position of phenol, which binds an A ring to inner molecular aldehyde in a compound generated by the 4-8 reaction. Further, the present invention contemplates that the generated compound by the 4-8 reaction can be synthesized based on the polycondensation reaction of general formula 4, and general formula 5 via a compound of general formula 3. Then the total synthesis of Et 743, which is the aimed compound, can be accomplished by way of the compounds represented by general formulae 5, 4, 3, 2 and 1 and the specific structure of general formulae 1 and 2. This synthetic route provides for the analogous compounds of Et 743.

DISCLOSURE OF THE INVENTION

The first embodiment of the present invention is an intermediate compound for total synthesis of ecteinascidins comprising, a compound represented by general formula 1 having a thioether group at $C_4$ site, and the substituent $R_2$ of $N_{12}$ site is trichloroethoxycarbonyl (Troc) to which various substituents can be introduced by mild conditions, and further having a 10 membered ring structure which can be converted to a ring of other numbered members,

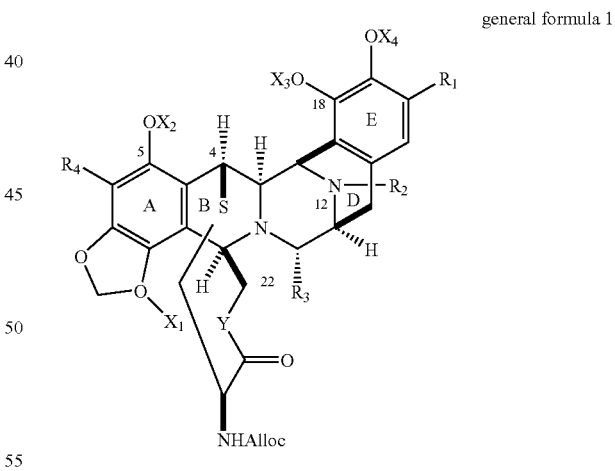

general formula 1 wherein, Y is O or NH, $X_2$, $X_3$ and $X_4$ are independently selected from the group consisting of H or an alkyl group of carbon number 4 or less, an alkoxyalkyl group, an allyl group, or an alkyl or arylsulfonyl group, $R_1$ and $R_4$ is H or an alkyl group of carbon number 4 or less, $R_2$ is an alkoxycarbonyl group which can be substituted by halogen, a lower alkyl sulfonyl group or an aryl sulfonyl group and $R_3$ is nitrile or OH.

The second embodiment of the present invention is a method for synthesis of the compound of general formula 1 comprising the processes displayed by the reaction 5-1, which is a transforming reaction of $C_{18}$ hydroxyl group to allyl ether and $C_{22}$ acetyl group to a hydroxyl group, the reaction 5-2, which is an introducing reaction of cysteine derivatives into $C_{22}$ acetyl group, and the reaction 5-3 which is a $C_4$ thioetherification reaction and a transforming reaction of $C_5$ hydroxyl group to an acetyl group, wherein Y is O, $X_2$ is Ac, $X_3$ is H, $R_1$ is Me, $R_2$ is Troc, $R_3$ is CN, and $X_4$ and $R_4$ are the same as in general formula 1.

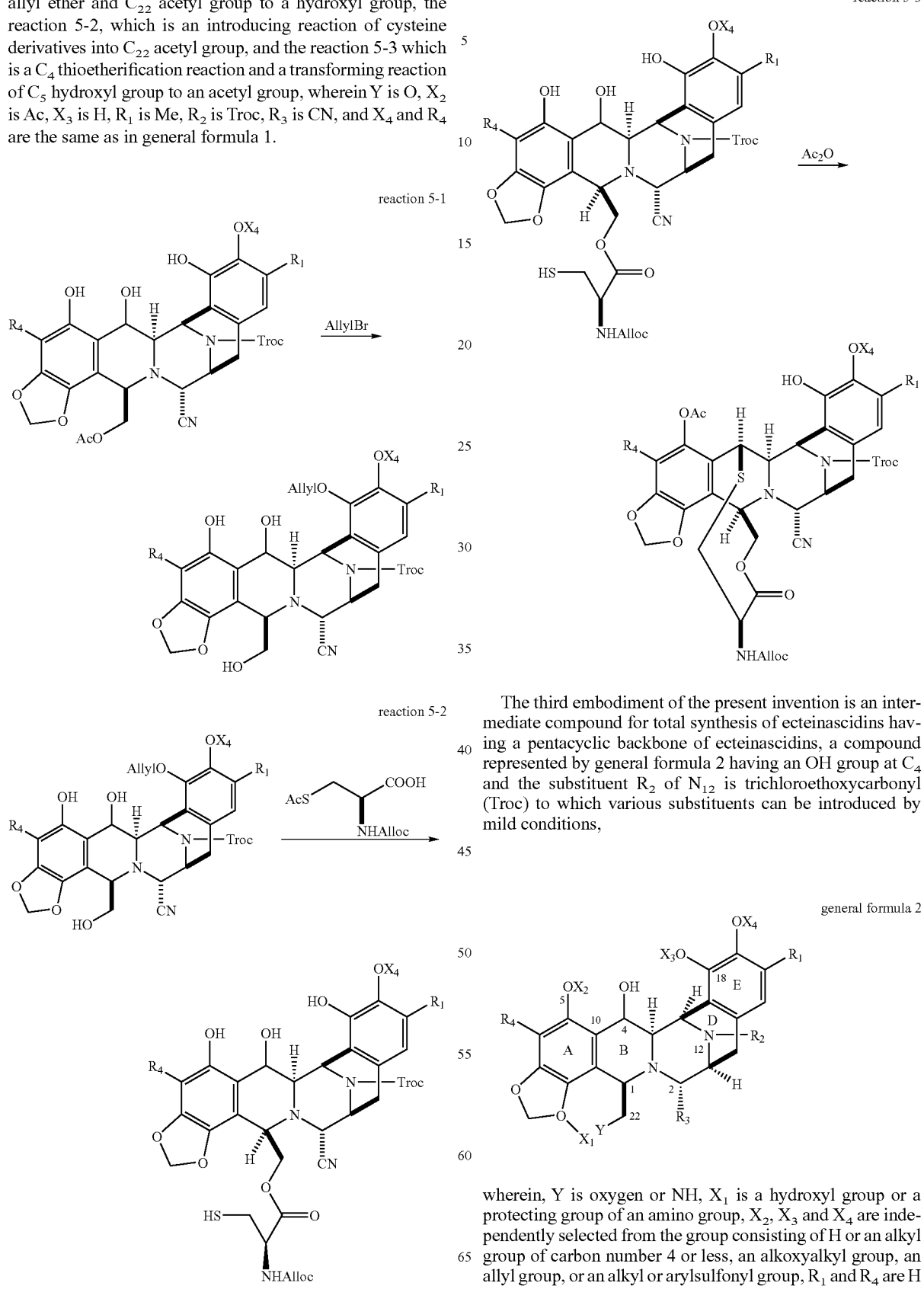

The third embodiment of the present invention is an intermediate compound for total synthesis of ecteinascidins having a pentacyclic backbone of ecteinascidins, a compound represented by general formula 2 having an OH group at $C_4$ and the substituent $R_2$ of $N_{12}$ is trichloroethoxycarbonyl (Troc) to which various substituents can be introduced by mild conditions, wherein, Y is oxygen or NH, $X_1$ is a hydroxyl group or a protecting group of an amino group, $X_2$, $X_3$ and $X_4$ are independently selected from the group consisting of H or an alkyl group of carbon number 4 or less, an alkoxyalkyl group, an allyl group, or an alkyl or arylsulfonyl group, $R_1$ and $R_4$ are H or an alkyl group of carbon number 4 or less, $R_2$ is an alkoxycarbonyl group which can be substituted by halogen, a lower alkyl sulfonyl group or an aryl sulfonyl group, and $R_3$ is nitrile or OH.

Desirably, the third embodiment of the present invention is the intermediate compound for total synthesis of ecteinascidins represented by general formula 2 wherein, Y is O, $X_1$ is selected from silyl groups consisting of an acyl group of carbon number 4 or less, TBDPS, TIPS, TBS, TES, and TMS, $X_2$ and $X_3$ are an allyloxy group, or an alkoxy group of carbon number 4 or less or an alkoxyalkoxy group, $R_3$ is CN and $R_4$ is an alkyl group of carbon number 4 or less.

The fourth embodiment of the present invention is a method for synthesis of the compound of general formula 2 consisting of the processes displayed by the reaction 4-1 which transforms $C_5$ mesily group to an acetyl group, the reaction 4-2 which is the transforming reaction of $N_{12}$ to T-butoxycarbonyl group to trichloroethyl group, the reaction of 4-3 which is a hydration reaction of $C_{3-4}$ double bond, the reaction 4-4 which is the transforming reaction of $C_4$ hydroxyl group to a TBS group and a transforming reaction of $C_{22}$ and $C_5$ acetyl group to a hydroxyl group, the reaction 4-5 which is a transforming reaction of $C_5$ hydroxyl group to a benzyl group, reaction 4-6 which is a reduction reaction of $C_{21}$ amide to a ring closing reaction of oxazolidine, the reaction 4-7 which is a ring operation reaction of oxazolidine and a transforming reaction of $C_2$ hydroxyl group to an aldehyde and the reaction 4-9 which is a transforming reaction of $C_5$, $C_{18}$ benzyloxy groups to a hydroxyl group and a ring forming reaction of the B ring, wherein Y is O, $X_2$ is H, $X_3$ is H, $R_3$ is CN, $X_1$ is Ac, $X_4$, $R_1$ and $R_4$ are the same as in the general formula 2.

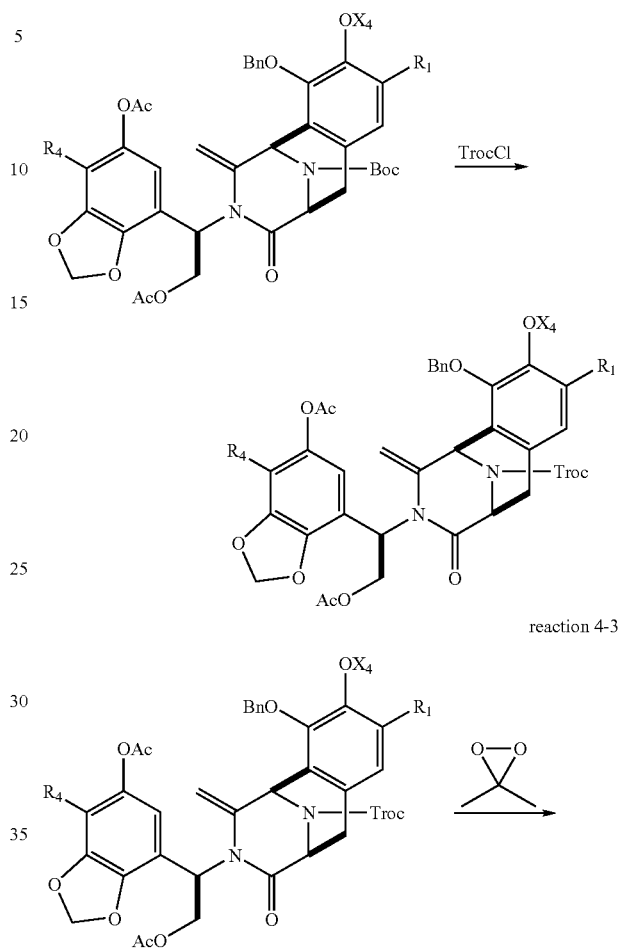

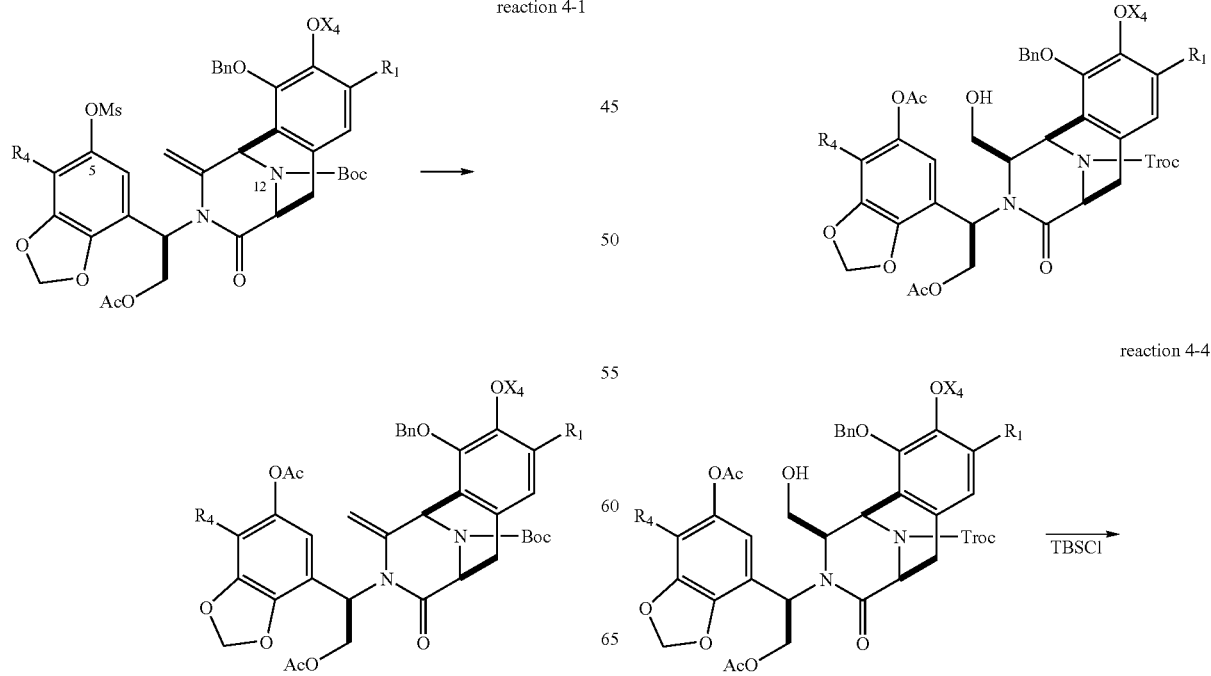

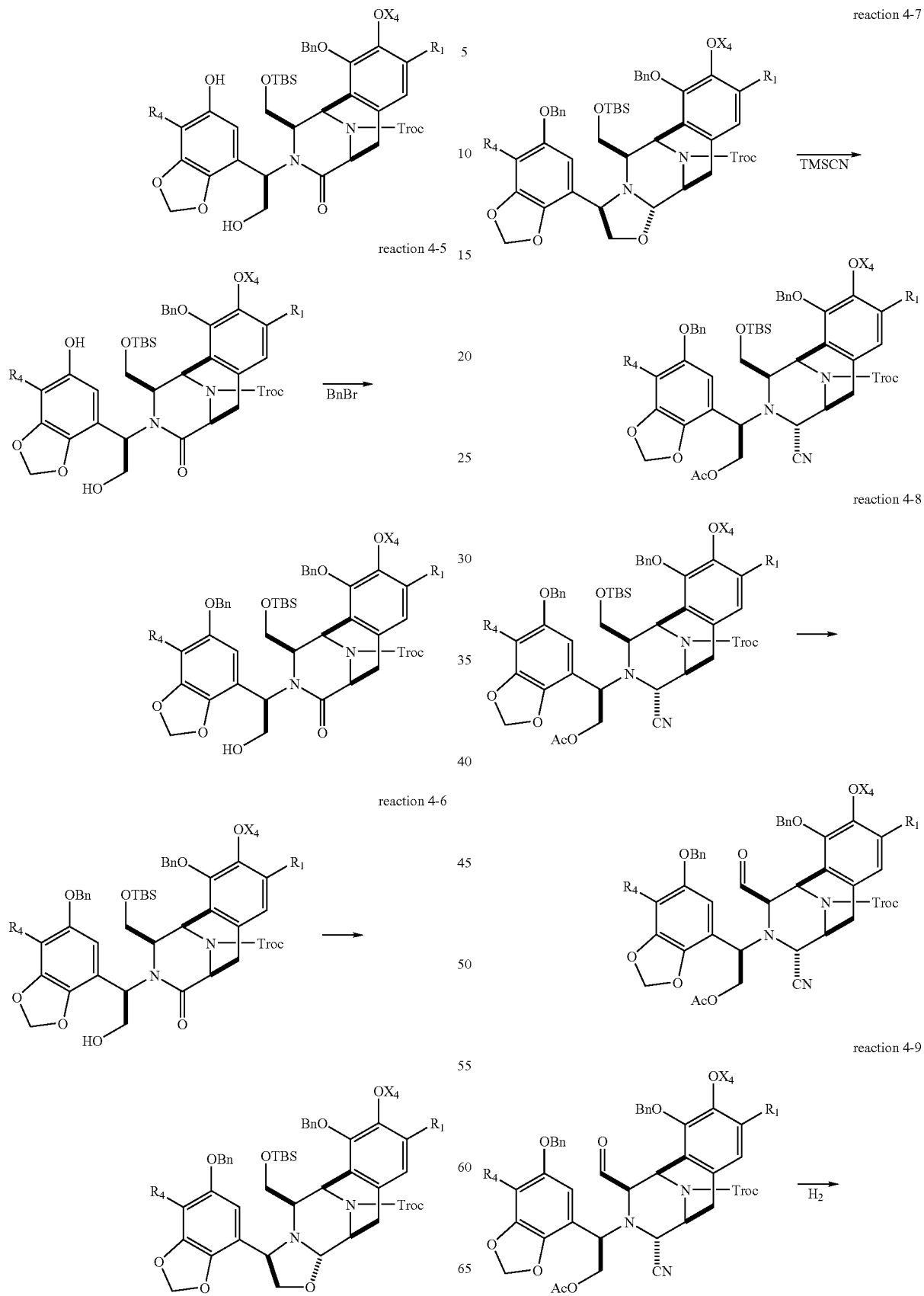

-continued

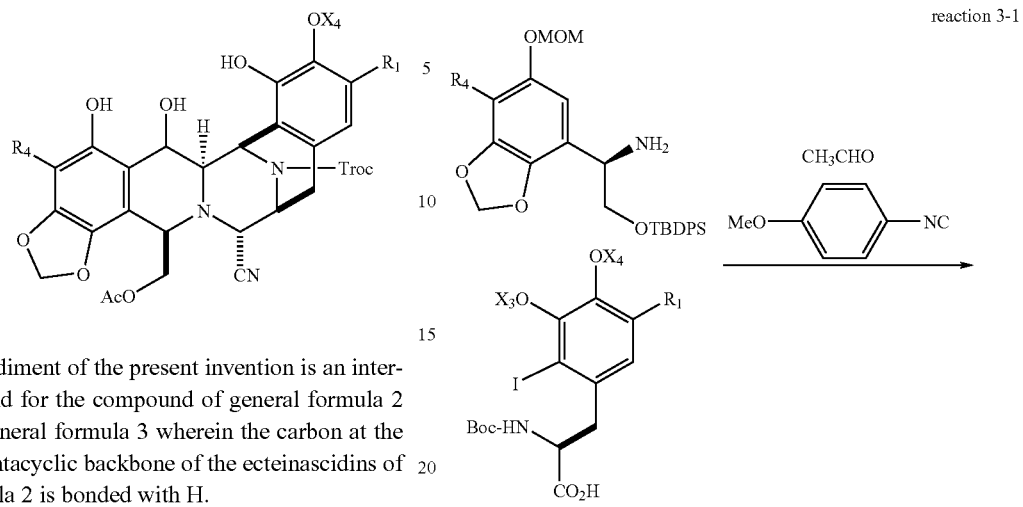

The fifth embodiment of the present invention is an intermediate compound for the compound of general formula 2 represented by general formula 3 wherein the carbon at the $C_{10}$ site of the pentacyclic backbone of the ecteinascidins of the general formula 2 is bonded with H.

general formula 3

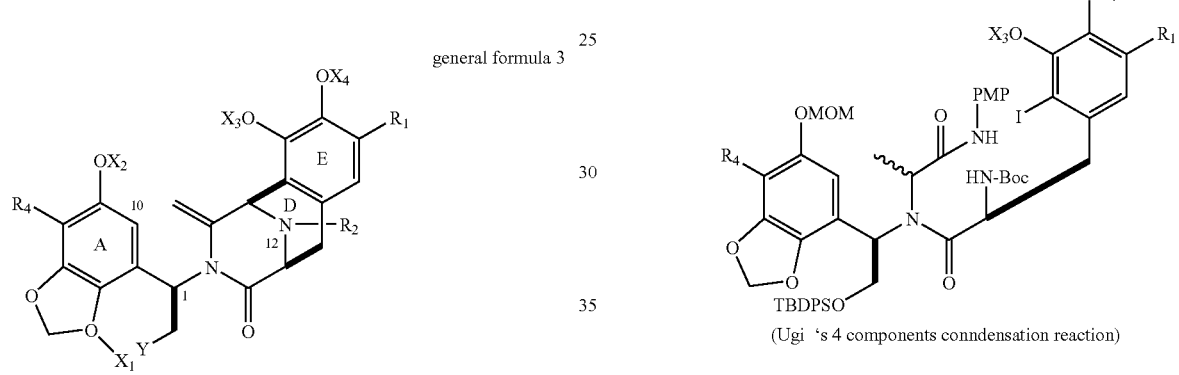

In general formula 3, $R_1$, $R_2$ and $R_4$, $X_1$-$X_4$ are the same as in general formula 2.

Desirably, the fifth embodiment of the present invention is the intermediate compound for the compound represented by general formula 3, wherein Y is O, $X_1$ is selected from the silyl groups consisting of an acyl group of carbon number 4 or less, TBDPS, TIPS, TBS, TES and TMS, $X_2$ and $X_3$ are an allyloxy group, or an alkoxy group of carbon number 4 or less, or an alkoxyalkoxy group, —$R_3$ is CN and $R_4$ is an alkyl group of carbon number 4 or less.

The sixth embodiment of the present invention is the method for synthesis of the compound of general formula 3 consisting of the processes displayed by the reaction 3-1 which is Ugi's 4 component condensation reaction, the reaction 3-2 which is the transforming reaction of the $C_{22}$ TBTPS group to an acetyl group, the reaction 3-3 which is a C ring formation reaction, the reaction 3-4 which is a transforming reaction of $C_5$ hydroxyl group to a mesyl group, the reaction 3-5 which is a reduction of $C_{11}$ amide and a dehydration reaction of $C_{3-4}$ double bond and the reaction 3-6 which is the construction of D ring by a Heck reaction, wherein Y is O, $X_1$ is Ac, $X_2$ is Ms and $R_2$ is Boc, $X_3$, $X_4$, $R_1$ and $R_4$ are same as to the general formula 2.

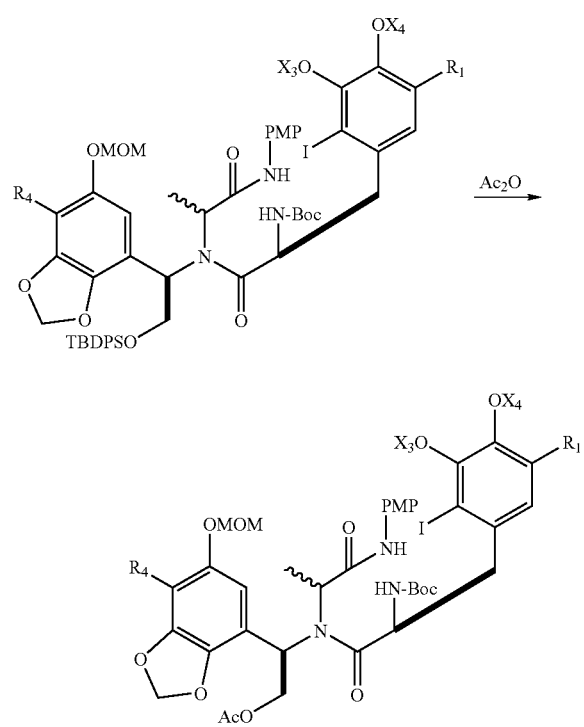

-continued reaction 3-3

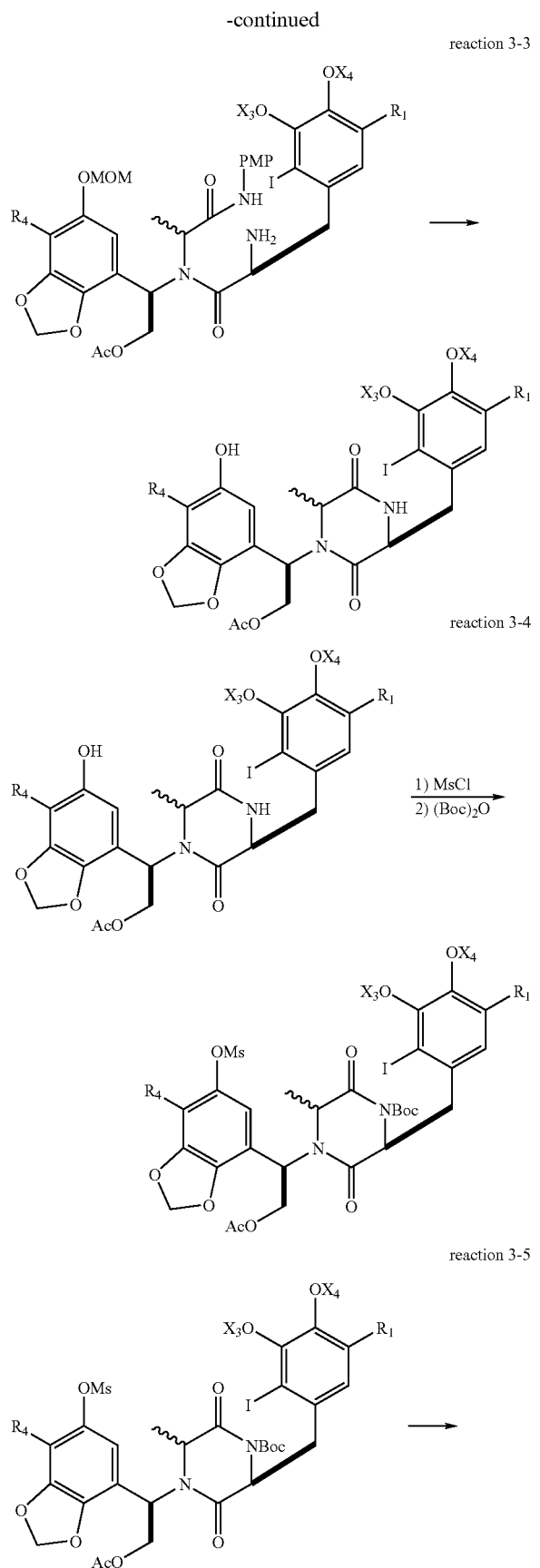

reaction 3-4

1) MsCl
2) (Boc)₂O reaction 3-5

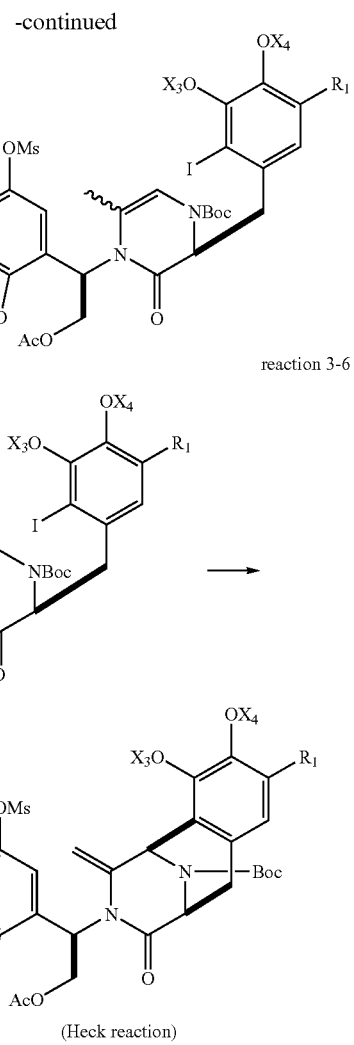

reaction 3-6

(Heck reaction)

The seventh embodiment of the present invention is the amine compound which provides a segment forming a chemical structure site of the A ring side of the intermediate compound of general formula 3 represented by general formula 4 by Ugi reaction.

general formula 4

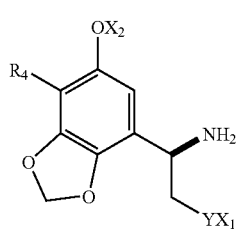

In general formula 4, $R_4$, $X_2$, Y and $X_1$ are the same as in general formula 2.

Desirably, the seventh embodiment of the present invention is the amine compound, wherein Y is O, $X_1$ is selected from the group of silyl groups consisting of an acyl group of carbon number 4 or less, TBDPS, TIPS, TBS, TES and TMS.

The eighth embodiment of the present invention is a method for synthesis of the compound of general formula consisting of the processes displayed by the reaction 2-1 which is the transforming reaction from $C_5$ hydroxyl group to a methoxymethyl group, reaction 2-2 which is the introducing reaction of a hydroxyl group to $C_{22}$, reaction 2-3 which is the Mannich reaction, reaction 2-4 which is the transforming reaction of $C_6$ hydroxyl group to a trifluoromethanesulfonyl group (Tf), reaction 2-5 which is the reducing reaction of lactone, reaction 2-6 which is the transforming reaction of $C_{22}$ hydroxyl to a TBDPS group, reaction 2-7 which is the methylatino reaction of $C_6$ to a TfO group and the reaction 2-8 which is the transforming reaction to amine, wherein Y=O, X, is TBDPS, $X_2$ is MOM and $R_4$ is Me.

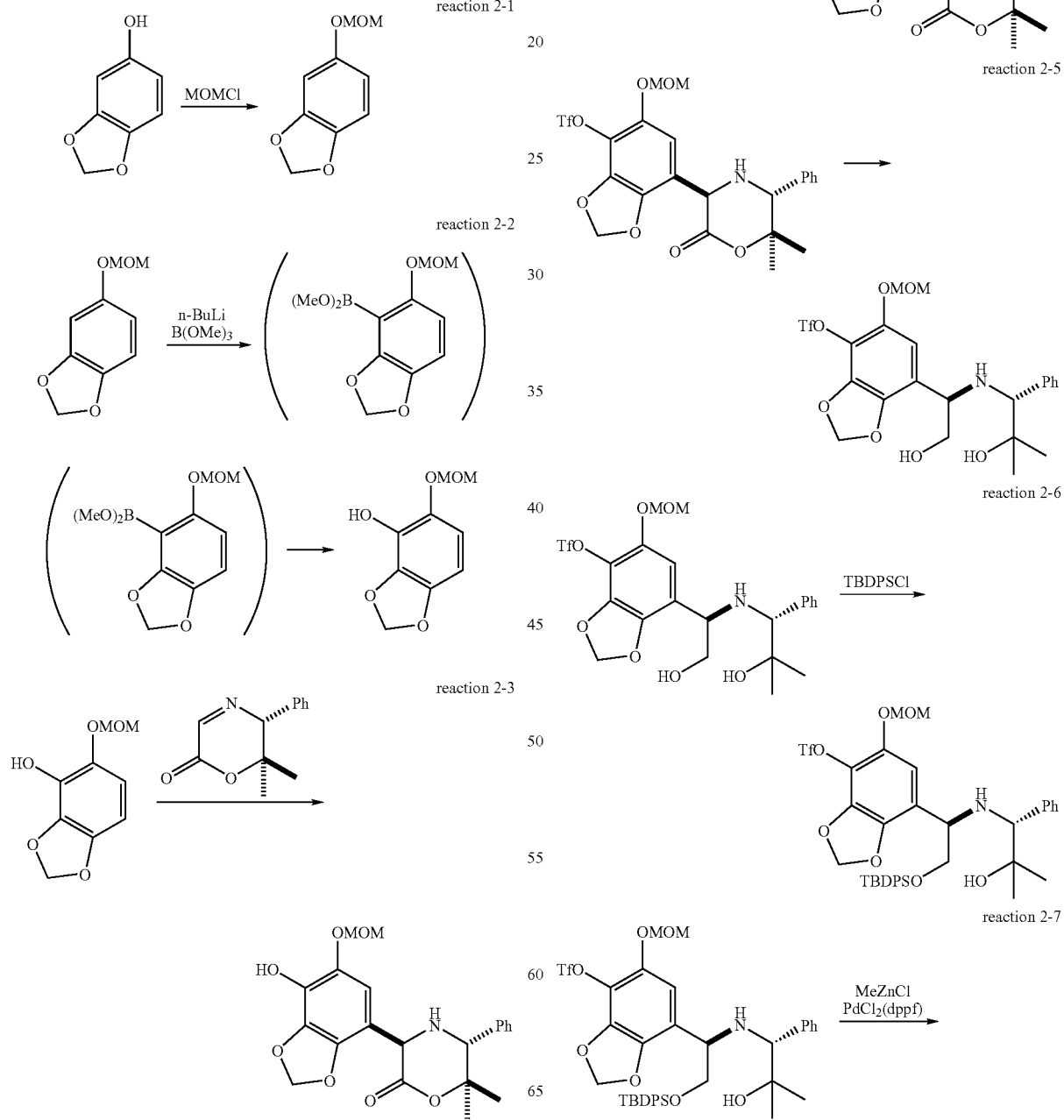

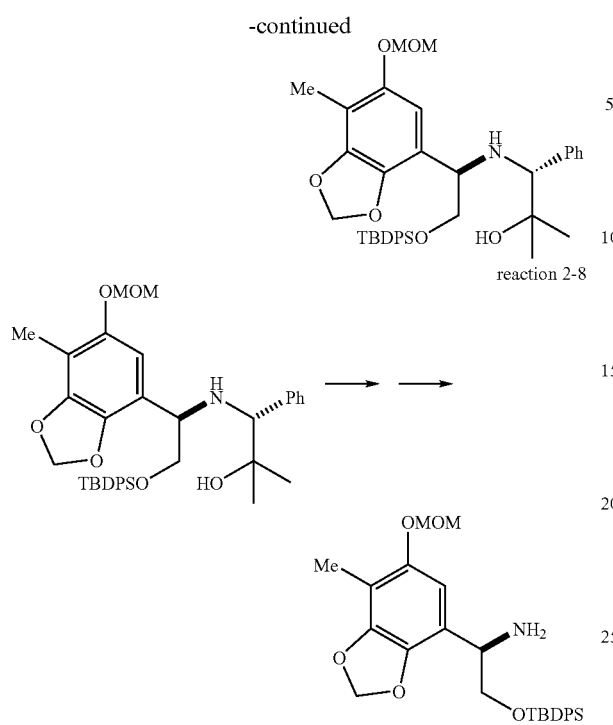

reaction 2-8

The ninth embodiment of the present invention is the carboxylic acid compound which provides a segment forming a chemical structural site on the ring side of the intermediate compound of general formula 3 represented by general formula 5 by Ugi reaction.

general formula 5

In general formula 5, $R_1$, $R_2$, $X_3$ and $X_4$ are the same as in general formula 1.

Desirably, the ninth embodiment of the present invention is the carboxylic acid compound wherein, $X_3$ and $X_4$ are independently selected from the group consisting of H or an alkyl group of carbon number 4 or less, an alkoxyalkyl group, an allyl group, an alkyl or arylsulfonyl group, $R_2$ is an alkoxycarbonyl group, a lower alkylsulfonyl or an arylsulfonyl group which can be substituted by halogen.

The tenth embodiment of the present invention is the method for synthesis of the compound of general formula 5 consisting of the processes displayed by the reaction 1-1 which is the introducing reaction of a formyl group to $C_{20}$, the reaction 1-2 which is the transforming reaction of the $C_{20}$ formyl group to dimethylacetal, the reaction 1-3 which is the iodination reaction of $C_{19}$ and an acidic hydrolysis reaction, the reaction 1-4 which is the transforming reaction of $C_{18}$ hydroxyl group to a benzyl group, the reaction 1-5 which is an Honor-Emons reaction, reaction 1-6 which is the asymmetric reducing reaction by a Duphos-Rh synthetic catalyst and reaction 1-7 which is the hydrolysis reaction of methylester, wherein $R_2$ is Boc, $X_3$ is Bn, $X_4$ is Me, the ring and $R_1$ is the same in general formula 2.

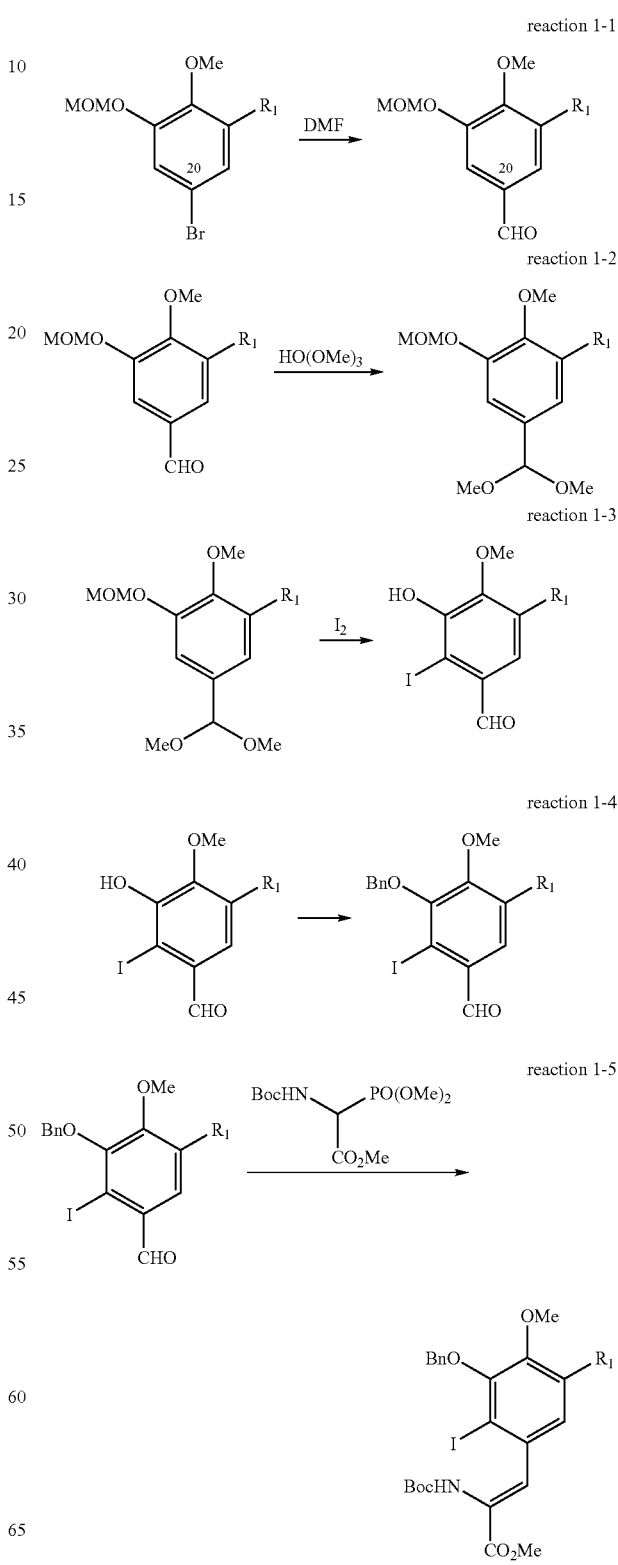

-continued

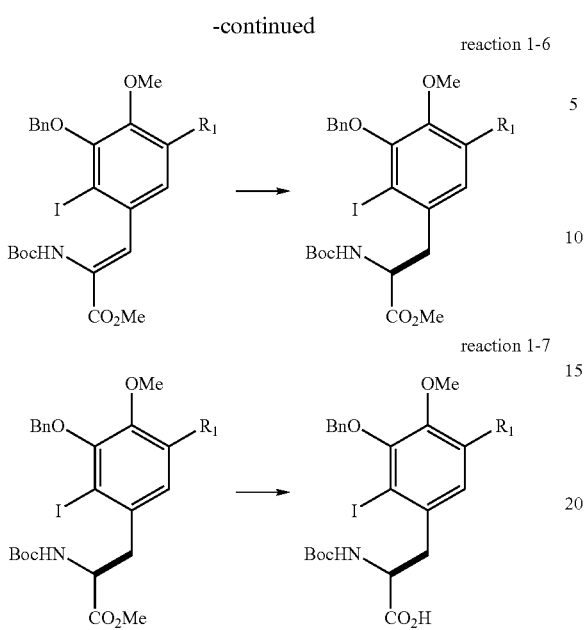

reaction 1-6 reaction 1-7

DESCRIPTION OF THE PREFERRED EMBODIMENT

The present invention will be illustrated more in detail according to the following description.

A. As mentioned above, the first feature of the present invention is the B ring forming reaction at the ortho position of phenol which binds A ring to aldehyde by reaction 4-9 in the synthesis process of the compound of the general formula 2. The feature of this reaction is that the reaction is progressed by a mild, neutralized condition. Having an OH group at the $C_4$ site which is expressed as the structural feature of the compound represented by general formula 2, the mild reaction condition is superior. Since the compound disclosed in the above-mentioned prior art has hydrogen at this site, a reaction under harsh conditions is required. Furthermore, from this intermediate synthesis, the synthesis of various analogous compounds is possible, and it is possible to obtain a compound having antineoplastic activity, such as au phtharasacidin being equal to Et 743.

B. The second feature of the present invention requires using the Ugi's 4 component reaction and the Heck reaction of reaction 3-6 as the key process. First, in the Ugi's 4 component condensation reaction of reaction 3-1, no condensation reagents are required for the generation of an amide bone. The compound of reaction 3-1 makes it possible to progress easily to the formation of the C ring of reaction 3-3. The ring forming reaction of reaction 3-6 not only controls the stereochemistry of $C_3$ site perfectly, but also can be performed using a catalytic amount of $Pd_2(dba)_3$, which is an expensive reagent, by catalytic amount.

C. The third feature of the present invention is that the amine represented by general formula 4 and the carboxylic acid represented by general formula 5 can be made by large scale production.

D. The fourth feature of the present invention is the ring forming reaction of a 10 membered ring shown by the reaction 5-3 process that is caused by bonding of a sulfur atom at the $C_4$ site. In the compound of the present invention, a hydroxyl group is introduced to the $C_4$ site, and it is possible to generate a cation of the benzyl site easily under the acidic condition. Therefore, the ring formation of a 10 membered ring by bonding the sulfur atom to said cation is produced with high yield. When compared with the case which uses the compound whose $C_4$ site is H, reported by Prof. E. J. Corey, the method of the present invention can use a more mild condition. Therefore, the method of the present invention has the advantage of easily accomplishing larger scale production, and further has the capability of introducing the ring of various numbers of members and is useful for the synthesis of various derivatives.

EXAMPLE

The present invention will be illustrated more in detail according to the specified Examples. However, these Examples are intended to provide easily understanding of the present invention and are not intending to limit the scope of the claim of the present invention.

Example 1

The synthesis of compound 2-8, wherein Y contained in general formula 4 is O, $X_1$ contained in general formula 4 is TBDPS, $X_2$ contained in general formula 4 is MOM and $R_4$ contained in general formula 4 is Me. The reaction process and the whole chemical formula of the generated compounds in each reaction process are shown by the following synthesis process A.

Synthesis Process A

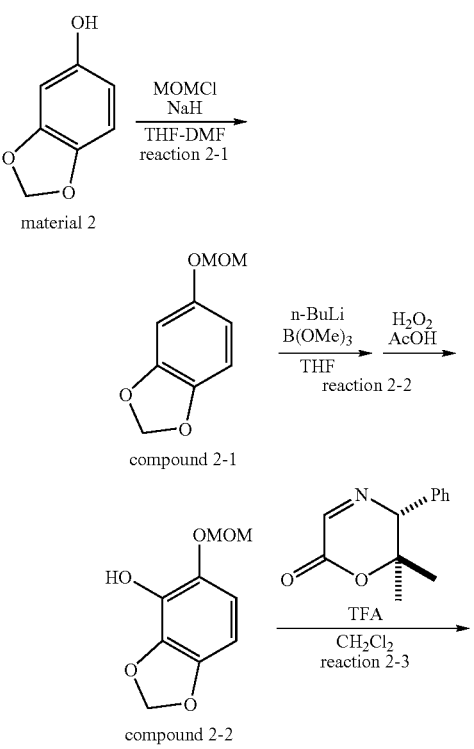

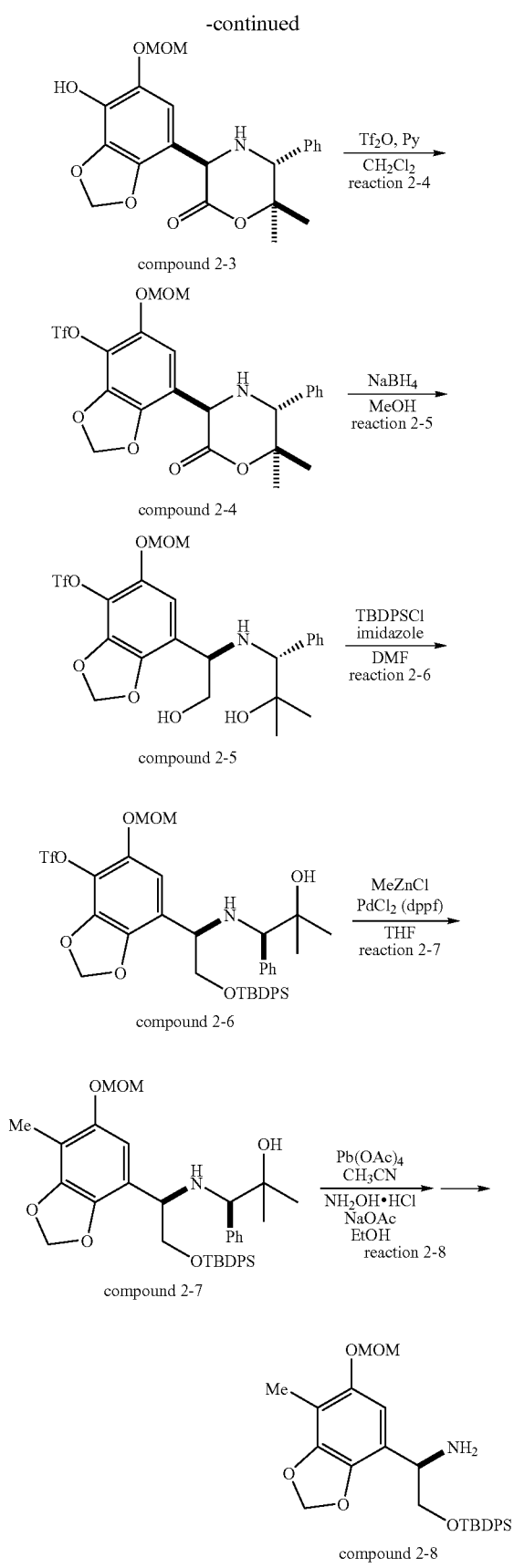

Detail of Synthetic Process A (1) Synthesis of Compound 2-1

NaH (40 g, 1.0 mol) was dispersed in 700 ml of the mixed solution of THF and DMF (5:2), THF solution (300 ml) of 3,4-methylenedioxyphenol (138 g, 1.0 mol) was dropped at 0° C. After stirred at room temperature for 30 minutes, MOMCl (84.5 g, 1.05 mol) was dropped and stirred at room temperature for 1 hour. Hexane and water were added to the reaction solution and the organic layer was separated. After the water layer was extracted by hexane, the organic layer was concentrated by vacuum. The residue was dissolved in hexane, washed by brine, then dried by $Na_2SO_4$. After concentrated by vacuum, the residue was distilled by vacuum (103° C./0.35 mmHg), and the compound 2-1 (177 g, 0.97 mol, 97%) was obtained as a colorless oil. The physical property of compound 2-1 is shown in Table 1.

TABLE 1

| Compound 2-1 |
| --- |
| IR (neat film) 1244, 1215, 1176, 1153, 1099, 1069, 1040, 1004, 940, 922, 842, 813 cm$^{-1}$; $^1$H NMR (400 MHz, CDCl$_3$) δ 6.71 (d, J = 8.4 Hz, 1H) 6.63 (s, 1H), 6.49 (d, J = 8.4 Hz, 1H), 5.90 (s, 2H), 5.08 (s, 2H), 3.46 (s, 3H); $^{13}$C NMR (100 MHz, CDCl$_3$), δ 152.5, 148.1, 142.5, 108.4, 108.0, 101.2, 99.7, 95.4, 55.8. |

Synthesis of Compound 2-2

After n-BuLi (3.02 mol n-hexane solution, 11.0 ml, 33.2 mmol) was dropped in THF (100 ml) solution of compound 2-1 (5.44 g, 29.9 mmol) at 0° C., the temperature was elevated to room temperature. The reaction solution was cooled down to 0° C., B(OOMe)$_3$ (4.10 ml, 36.1 mmol) was added, then AcOH(3.4 ml, 59 mmol) and aqueous solution of 7% $H_2O_2$ (26 ml, 60 mmol) were added. The reaction solution was stirred for 4.5 hours at room temperature, saturated aqueous solution of (NH4)$_2$SO$_4$ (100 ml) and saturated aqueous solution of Na$_2$SO$_3$(100 ml) were added, and an organic layer was dried with MgSO$_4$ then concentrated by vacuum. The residue was purified by silica gel chromatography (70% EtOAc in n-hexane), and the compound 2-2 (5.42 g 27.3 mmol) was obtained as a colorless oil. The physical property of compound 2-2 is shown in Table 2.

TABLE 2

| Compound 2-2 |
| --- |
| IR (neat film) 3439, 1652, 1493, 1292, 1245, 1157, 1044, 932, 791 cm$^{-1}$; $^1$H NMR (400 MHz, CDCl$_3$) δ 6.55 (d, J = 8.4 Hz, 1H), 6.45 (br, 1H), 6.32 (d, J = 8.4 Hz, 1H), 5.94 (s, 2H), 5.09 (s, 2H), 3.50 (s, 3H); $^{13}$C NMR (100 MHz, CDCl$_3$) δ 144.3, 141.3, 134.4, 132.0, 109.2, 101.6, 99.1, 97.3, 60.4, 56.3 |

Synthesis of Compound 2-3

As the method for synthesis of agent lactone (agent-1) which is added in the reaction 2-3, document, for example, ["Synthesis of Optically Active Arylglycines; Stereoselective Mannich Reaction of Phenols with a New Chiral template," S. Tohma, A. Endo, T. Kan, T. Fukuyama, Synlett, 1479-1499 (2001).] can be mentioned.

In CH$_2$Cl$_2$ (200 ml) solution of the compound 2-2 (19.8 g, 100 mmol) and agent-1 (20.3 g, 100 mmol), TFA (38 ml, 0.49 mol, 5 equiv) was dropped by 1.5 hours at −10° C. After the reaction solution was stirred for 40 minutes at room temperature, $Na_2CO_3$ (40 g, 0.38 mol, 3.8 equivalent) and $H_2O$ (200 ml) were added and extracted by $CH_2Cl_2$. The water layer was extracted by $CH_2Cl_2$, then the organic layer was washed by brine, dried by $Na_2SO_4$ and concentrated by $CH_2Cl_2$. The residue was purified by silica gel chromatography (30% EtOAc in n-hexane), and the compound 2-3 (35.6 g 89 mmol, 89%) was obtained a colorless oil. The physical property of compound 2-3 is shown in Table 3.

TABLE 3

Compound 2-3

$[\alpha]D^{27}$ −75.2° (c = 1.65, $CHCl_3$); IR (neat film) 3327, 1724, 1506, 1457, 1299, 1151, 1118, 1082, 1049, 1101, 934 $cm^{-1}$; $^1H$ NMR (400 MHz, $CDCl_3$) δ 9-7.37 (m, 5H), 6.51 (s, 1H) 5.93 (s, 1h), 5.91 (d, J = 8.0 Hz, 1H), 5.05 (d, J = 8.0 Hz, 1H), 5.03 (s, 1H) 415 (s, 1H), 3.51 (s, 3H), 2.03 (br, 1H), 1.37 (s, 6H); $^{13}C$ NMR (100 MHz, $CDCl_3$) δ 169.0, 141.8, 141.4, 138.2, 134.8, 132.4, 128.4, 128.3, 128.3, 111.6, 110.0, 101.9, 86.7, 61.0, 57.1, 56.4, 26.6, 22.0;

Synthesis of Compound 2-4

To the solution of the compound 2-3 (242 mg, 0.603 mmol) and pyridine (0.15 ml, 1.9 mmol), $Tf_2O$ (0.13 ml, 0.77 mmol, 1.3 equivalent) was dropped at 0° C. After the reacted product was stirred for 5 minutes, the aqueous solution of saturated $NaHCO_3$ was added and extracted by EtOAc. The organic layer was washed by the aqueous solution of 1N HCl and the saturated aqueous solution of $NaHCO_3$, then dried by $MgSO_4$ and concentrated by vacuum. The residue was purified by silica gel chromatography (in 50% EtOAc n-hexane), and the compound 2-4 (290 mg, 0.544 mmol, 90%) was obtained as a colorless oil. The physical properties of the compound 2-4 are shown in Table 4.

TABLE 4

Compound 2-4

$[\alpha]D^{26}$ −32.1° (c = 2.59, $CHCl_3$); IR (neat film) 3333, 1733, 1496, 1462, 1427, 1299, 1216, 1138, 1056, 999, 979, 936, 832 $cm^{-1}$; $^1H$ NMR (400 MHz, $CDCl_3$) δ 7.32-7.40 (m, 5H), 6.71 (s, 1H) 6.06 (s, 1H), 6.03 (s, 1H), 5.19 (d, J = 5.8 Hz, 1H), 5.14 (d, J = 5.8 Hz, 1H), 5.09 (s, 1H) 4.23 (s, 1H), 3.49 (s, 3H), 2.01 (br, 1H), 1.40 (s, 6H); $^{13}C$ NMR (100 MHz, $CDCl_3$) δ 167.8, 144.9, 141.2, 140.2, 137.8, 128.3, 128.2, 128.1, 123.1, 120.2, 116.7, 108.0, 103.1, 95.9, 86.7, 61.3, 56.9, 56.3, 26.4, 21.8

Synthesis of Compound 2-5

To the MeOH (50 ml) solution of the compound 2-4 (4.70 g, 8.8 mmol), $NaBH_4$ was added at 0° C. and stirred for 30 minutes. To the reaction solution, EtOAc (300 ml) was added and washed by 1N HCl (100 ml). The organic layer was washed by saturated aqueous solution of $NaHCO_3$, and after dried by $MgSO_4$, concentrated by vacuum. The residue was purified by silica gel chromatography (in 60% EtOAc n-hexane), and the compound 2-5 (4.04 g, 7.5 mmol, 85%) was obtained as a colorless oil. The physical properties of the compound 2-5 are shown in Table 5.

TABLE 5

Compound 2-5

$[\alpha]D^{27}$ −102° (c = 1.67, $CHCl_3$); IR (neat flim) 3398, 1497, 1456, 1426, 1218, 1136, 1054, 937, 833 $cm^{-1}$; 1H NMR (400 MHz, $CDCl_3$) δ

TABLE 5-continued

Compound 2-5

7.25-7.33 (m, 5H), 6.63 (s, 1H) 5.94 (s, 1H), 5.93 (s, 1H), 5.11 (d, J = 6.8 Hz, 1H), 5.07 (d, J = 6.8 Hz, 1H), 3.65 (br, 1H), 3.52-3.64 (br, 2H), 3.50 (s, 3H), 3.39 (s, 1H), 2.71 (br, 1H), 1.11 (s, 6H); $^{13}C$ NMR (100 MHz, $CDCl_3$)δ 144.8, 141.6, 139.9, 139.2, 128.7, 128.1, 127.5, 122.4, 120.9, 120.1, 116.9, 107.1, 102.9, 95.6, 72.7, 68.9, 64.9, 56.9, 56.3, 27.9, 23.8;

Synthesis of Compound 2-6

To DMF solution of the compound 2-5 (1.00 g, 1.86 mmol) and imidazole (0.63 g, 9.3 mmol), TBDPSCl (1.22 ml, 4.7 mmol) was added and stirred at room temperature. To the reacted product, $Et_2O$ and water were added and the organic layer was washed by brine, dried by $Na_2SO_4$ and concentrated by vacuum. The residue was purified by silica gel chromatography (in 10% EtOAc n-hexane), and the compound 2-6 (1.31 g, 1.69 mmol, 91%) was obtained as a colorless oil. The physical properties of the compound 2-6 are shown in Table 6.

TABLE 6

Compound 2-6

$[\alpha]D^{27}$ −75.2°(c = 1.65, $CHCl_3$); IR (neat film) 3445, 1469, 1428, 1363, 1263, 1109, 1062, 991, 944, 826 $cm^{-1}$; $^1H$ NMR (400 MHz, $CDCl_3$)δ 7.61 (d, J = 8.0 Hz, 2H), 7.56 (d, J = 8.0 Hz, 2H), 7.23-7.42 (m, 11H), 6.62 (s, 1H), 5.83 (s, 2H), 5.10 (d, J = 6.8 Hz, 1H), 5.08 (d, J = 6.8 Hz, 1H), 3.77 (dd, J = 6.0, 6.8 Hz, 1H), 3.67 (m, 2H), 3.47 (s, 3H), 3.37 (s, 1H), 3.34 (br, 1H), 1.909 (s, 6H), 1.08 (s, 9H); $^{13}C$ NMR (100 MHz, $CDCl_3$)δ 144.7, 141.8, 139.8, 139.5, 135.6, 132.9, 129.7, 128.5, 128.1, 127.7, 127.6, 127.4, 122.5, 121.0, 120.1, 116.9, 107.7, 102.7, 95.8, 72.2, 68.6, 66.4, 56.8, 56.3, 27.4, 26.8, 24.2, 19.2;

Synthesis of Compound 2-7

To the THF (105 ml) solution of the compound 2-6 (16.7 g, 21.5 mmol), MeZnCl (2.0M in THF solution, 37.5 ml, 75.1 mmol) was added at 0° C. After the temperature of the reaction solution was elevated to room temperature, $PdCl_2$ (dppf) (314 mg, 0.43 mmol) was added and refluxed by heating for 13.5 hours. EtOAc was added to the reaction solution, then washed by 1N HCl aqueous solution, saturated aqueous solution of $NaHCO_3$ and brine. The organic layer was dried by $Na_2SO_4$ and concentrated by vacuum. The residue was purified by silica gel chromatography (in 10% EtOAc n-hexane), and the compound $2^{-7}$ (13.4 g, 20.9 mmol, 97%) was obtained as a white solid. The physical properties of the compound 2-7 are shown in Table 7.

TABLE 7

Compound 2-7

$[\alpha]D^{26}$ −99.3° (c = 0.81, $CHCl_3$); IR (neat film) 3457, 2931, 1494, 1457, 1427, 1362, 1216, 1139, 1110, 1056, 1006, 936, 828 $cm^{-1}$; $^1H$ NMR (400 MHz, $CDCl_3$ δ 7.63 (d, J = 6.8 Hz, 2H), 7.56, (d, J = 6.8 Hz, 2H), 7.22-7.47 (m, 11H), 6.30 (s, 1H), 5.77 (s, 2H), 5.03 (d, J = 5.6 Hz, 1H), 5.01 (d, J = 5.6 Hz, 1H), 3.83 (dd, J = 10.8, 10.8, 1H), 3.61-3.66 (m, 2H), 3.44 (s, 3H), 3.38 (s, 1H), 2.08 (s, 3H), 1.09 (s, 9H), 1.06 (s, 6H); $^{13}C$ NMR (100 MHz, $CDCl_3$) δ 150.8, 146.6, 140.0, 139.7, 135.6, 135.6, 133.2, 133.1, 130.9, 130.4, 130.0, 129.7, 129.6, 128.5, 128.4, 128.0, 127.7, 127.6, 127.2, 117.7, 109.6, 107.0, 100.8, 95.6, 72.1, 68.5, 66.6, 57.7, 56.0, 27.3, 26.8, 24.0, 19.2, 8.8

Synthesis of Compound 2-8

To the CH₃CN (12 ml) solution of the compound 2-7 (640 mg, 1.0 mmol), Pb(OAc)₄ (0.56 g, 1.26 mmol) was added slowly at 0° C. To the reaction solution, saturated aqueous solution of NaHCO₃ was added and extracted by EtOAc. The organic layer was washed by brine, dried by Na₂SO₄, concentrated by vacuum and crude product was obtained. The obtained crude product was dissolved in EtOH (10 ml), then hydrochloric acid salt of hydroxylamine (347 mg, 5.6 mmol) and sodium acetate (410 mg, 5.0 mmol) were added at room temperature and stirred for 1.5 hours. EtOAc was added to the reaction solution, then filtrated by celite and concentrated by vacuum. The residue was dissolved with EtOAc and washed by 1N HCl aqueous solution, saturated aqueous solution of NaHCO₃ and brine. After the organic layer was dried by Na₂SO₄, concentrated by vacuum. The residue was purified by silica gel chromatography (EtOAc), and the compound 2-8 (436 mg, 0.88 mmol, 89%) was obtained. The physical properties of the compound 2-8 are shown in Table 8.

TABLE 8

| Compound 2-8 |
|---|
| $[\alpha]_D^{23}$ −1.99° (c = 1.30, CHCl₃); IR (neat film) 1440, 1115, 1062, 991, 938, 826 cm⁻¹; ¹H NMR (400 MHz, CDCl₃) δ 7.61-7.65 (m, 4H), 7.35-7.45 (m, 6H), 6.57 (s, 1H), 5.81 (s, 2H), 5.09 (s, 2H), 4.16 (dd, J = 6.8, 4.8 Hz, 1H), 3.87 (dd, J = 10.0, 4.8 Hz, 1H), 3.76 (dd, J = 10.0, 6.8 Hz, 1H), 3.48 (s, 3H), 2.14 (s, 3H), 1.08 (s, 9H); ¹³C NMR (100 MHz, CDCl₃) δ 150.8, 146.1, 139.1, 135.5, 135.5, 133.4, 133.3, 129.5, 129.5, 127.5, 120.7, 109.1, 105.8, 100.7, 95.7, 68.1, 55.9, 53.4, 26.7, 19.1, 8.8 |

Example 2

Synthesis of the Compound 1-7 Contained in General Formula 5

The process for synthetic reaction and the chemical structure of the products obtained at each process are totally shown in following synthesis process B.

Synthesis Process B

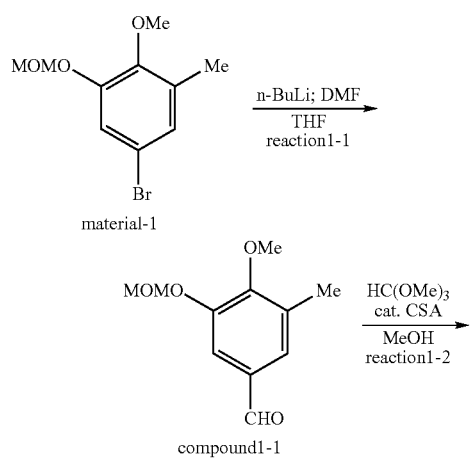

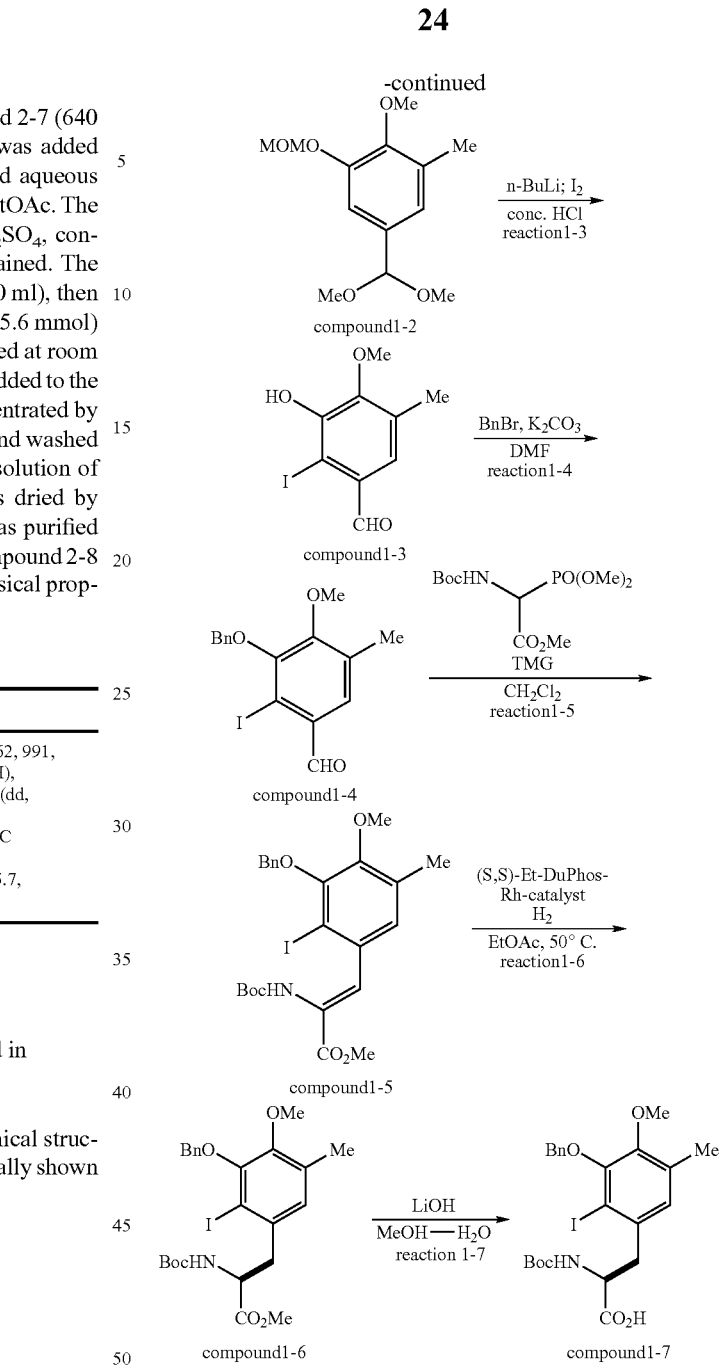

Detail of Synthesis of the Compound 1-7

Regarding the synthesis of bromide (starting material-1), for example, document of ["Synthetic Study on Ectenascidin 743 starting from D-glucose" A. Entoh, T. Kan, and T. Fukuyama, Synlett, 1103-1105 (1999)] can be mentioned.

Synthesis of Compound 1-1

To the THF solution (900 ml) of the starting material-1 (114 g, 437 mmol), n-BuLi (2.46M in n-hexane solution, 270 ml, 664 mmol) was added at −78° C., then DMF (170 ml, 2.20 mol) was added. The temperature of the reaction solution was elevated to room temperature, and water was added to the reaction solution, then concentrated by vacuum. Et$_2$O was added to the residue, and washed by saturated aqueous solution of NaHCO$_3$ and brine. After dried by MgSO$_4$, concentrated by vacuum. The residue was purified by silica gel chromatography (30% Et$_2$O in n-hexane), and the compound 1-1 (73.0 g, 347 mmol, 79%) was obtained as a colorless oil. The physical properties of the compound 1-1 are shown in Table 9.

TABLE 9

Compound 1-1

IR (neat film) 1699, 1585, 1488, 1451, 1382, 1299, 1235, 1155, 1133, 1099, 1051, 1003, 928, 863 cm$^{-1}$; $^1$H NMR (400 MHz, CDCl$_3$) δ 9.83 (s, 1H), 7.49 (s, 1H), 7.36 (s, 1H), 5.25 (s, 2H), 3.90 (s, 3H), 3.51 (s, 3H), 2.31 (s, 3H); $^{13}$C NMR (100 MHz, CDCl$_3$) δ 191.2, 153.5, 150.5, 132.8, 132.1, 126.9, 114.2, 95.0, 60.3, 56.3, 16.0

Synthesis of Compound 1-2

To the MeOH solution (5.0 ml) of the compound 1-1 (331 mg, 1.57 mmol) and CH(OMe)$_3$ (1.0 ml, 9.14 mol), CSA (20.2 mg, 0.09 mmol) was added and refluxed by heating for 1 hour. K$_2$CO$_3$ (103 mg, 0.75 mmol) was added to the reaction solution and concentrated by vacuum. The residue was dissolved in Et$_2$O and filtrated by a column of basic alumina. After concentrated by vacuum, the compound 1-2 (381 mg, 1.49 mmol, 94%) was obtained as a colorless oil. The obtained compound 1-2 was used to the next reaction without refining. The physical properties of the compound 1-2 are shown in Table 10.

TABLE 10

Compound 1-2

1H NMR (400 MHz, CDCl$_3$) δ 7.05 (s, 1H), 6.93 (s, 1H), 5.27 (s, 1H), 5.25 (s, 2H), 3.89 (s, 3H), 3.59 (s, 3H), 3.34 (s, 3H), 2.32 (s, 3H)

Synthesis of Compound 1-3

To the Et$_2$O solution (4.0 ml) of the compound 1-2 (38 mg, 1.49 mmol), n-BuLi (2.46M in n-hexane solution, 0.95 ml, 2.34 mmol) was added at 0° C., then the temperature was elevated to room temperature. After reduced the temperature of the reaction solution to 0° C., Et$_2$O (3.0 ml) solution of I$_2$ (648 mg, 2.55 ml) was added. After water and saturated aqueous solution of NaHCO$_3$ were added, extracted by EtOAc. The organic layer was washed by brine, dried by MgSO$_4$ and concentrated by vacuum. The residue was dissolved by THF (5.0 ml) and 12N HCl (2.0 ml) aqueous solution was added at room temperature. After stirred for 15 minutes, neutralized by saturated aqueous solution of NaHCO$_3$ and extracted by EtOAc. The organic layer was washed by saturated aqueous solution of brine, dried by MgSO$_4$ and concentrated. The residue was dissolved by CH$_2$Cl$_2$ and filtrated by silica gel and concentrated by vacuum. The obtained solid was washed by n-hexane and the compound 1-3 (314 mg, 1.07 mmol, 72%), and the compound 1-3 was obtained as a colorless solid. The physical properties of the compound 1-3 are shown in Table 11.

TABLE 11

Compound 1-3

IR (neat film) 3389, 1670, 1583, 1464, 1412, 1299, 1247, 1127, 997 cm$^{-1}$; $^1$H NMR 400 MHz, CDCl$_3$) δ 10.0 (s, 1H), 7.37 (s, 1H), 6.43 (bs, 1H), 3.89 (s, 3H), 2.32 (s, 3H); $^{13}$C NMR (100 MHz, CDCl$_3$) δ 194.9, 149.9, 149.2, 131.3, 130.9, 125.3, 125.3, 60.8, 15.8;

The Synthesis of Compound 1-4

To the CH$_3$CN (3.0 ml) solution of the compound 1-3 (325 mg, 1.11 mmol) and K$_2$CO$_3$ (465 mg, 3.37 mmol) BuBr (140 μl, 1.18 mmol) were added at room temperature and refluxed by heating for 40%. After CH$_2$Cl$_2$ were added to the reaction solution, filtrated by Celite, then concentrated by vacuum. The residue was purified by silica gel chromatography (50% CH$_2$Cl$_2$ in n-hexane), and the compound 1-4 (415 mg, 1.09 mmol, 98%) was obtained as a colorless oil. The physical properties of the compound 1-4 are shown in Table 12.

TABLE 12

Compound 1-4

IR (neat film) 1684, 1576, 1464, 1303, 1153, 1068, 1005 cm$^{-1}$; $^1$H NMR (400 MHz, CDCl$_3$) δ 10.0 (s, 1H), 7.60 (d, 8.0 Hz, 2H), 7.59 (s, 1H), 7.30-7.45 (m, 3H), 5.01 (s, 2H), 3.93 (s, 3H), 2.30 (s, 3H); $^{13}$C NMR (100 MHz, CDCl$_3$) δ 195.3, 157.1, 151.3, 136.3, 133.3, 131.3, 128.7, 128.5, 128.4, 128.2, 98.2, 74.9, 60.6, 15.7;

The Synthesis of Compound 1-5

To the CH$_2$Cl$_2$ solution (100 ml) of the compound 1-4 (8.30 g, 21.7 mmol) and methyl-2-butoxycarbonylamino-dimethylsulfonoacetate (7.76 g, 26.1 mmol), TMG (4.10 ml, 32.7 mmol) was added at room temperature and stirred for 24 hours at room temperature. The reaction solution was washed by 10% citric acid and saturated aqueous solution of NaHCO$_3$, then the organic layer was dried by MgSO$_4$ and concentrated by vacuum. The residue was purified by silica gel chromatography, and the compound 1-5 (11.2 g, 20.2 mmol, 1.93%) was obtained as a yellow crystal. The further refining was carried out by re-crystallization (EtOAc/n-hexane). The physical properties of the compound 1-5 are shown in Table 13.

TABLE 13

Compound 1-5

IR (neat film) 3336, 1717, 11457, 1367, 1249, 1160, 1065, 1003 cm$^{-1}$; $^1$H NMR (400 MHz, CDCl$_3$) δ 7.60 (d, J = 6.8 Hz, 2H), 7.36-7.60 (m, 3H), 7.24 (s, 1H), 7.20 (s, 1H), 5.00 (s, 2H), 3.88 (s, 3H), 3.86 (s, 3H), 2.23 (s, 3H); $^{13}$C NMR (100 MHz, CDCl$_3$) δ 165.6, 152.4, 151.6, 136.8, 134.2, 132.5, 131.7, 128.7, 128.4, 128.2, 126.8, 125.4, 96.9, 80.9, 74.6, 60.5, 52.7, 28.0, 15.8

The Synthesis of Compound 1-6

The EtOAC solution (30 ml) of frozen and degased compound 1-5 (5.04 g, 9.10 mmol) and Rh[(COD)-(S,S)-Et-DuPHOS]$^+$TfO— (99.0 mg, 0.14 mmol, 1.5 mol %) was poured into a high pressure reactor and stirred for 22 hours under hydrogen atmosphere of 500 atm at 50° C. The reaction solution was concentrated by vacuum and the residue was purified by silica gel chromatography (50% EtOAc in n-hexane), and the compound 1-6 (5.01 g, 902 mmol, 99%) was obtained as a light yellow crystal.

Wherein, (S,S)-Et-DuPhos-catalyst Rh{[(COD)-(S,S)-Et-DuPHOS]⁺TfO—} is shown as follows.

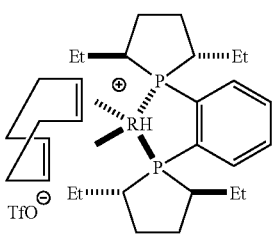

The physical properties of the compound 1-6 are shown in Table 14.

TABLE 14

| Compound 1-6 |
|---|
| $[\alpha]D^{27}$ +7.4° (c = 1.09, CHCl₃); R (neat film) 3374, 1764, 1711, 1510, 12457, 1363, 1162, 1068, 1003 cm⁻¹; ¹H NMR (400 MHz, CDCl₃) δ 7.60 (d, J = 8.8 Hz, 2H), 7.32-7.45 (m, 3H), 6.85 (s, 1H), 5.06 (d, J = 8.8 Hz, 1H), 4.99 (s, 1H), 4.62 (ddd, J = 9.2, 8.8, 5.6 Hz, 1H), 3.82 (s, 3H), 3.72 (s, 3H), 3.28 (dd, J = 14.4, 5.6 Hz, 1H), 3.09 (dd, J = 14.4, 9.2 Hz, 1H), 2.23 (s, 3H), 1.43 (s, 9H); ¹³C NMR (100 MHz, CDCl₃) δ 172.4, 154.9, 151.7, 150.4, 136.9, 135.4, 132.3, 128.6, 128.4, 128.1, 127.8, 97.0, 79.8, 74.5, 60.4, 53.8, 52.3, 42.7, 28.2, 15.6; |

The Synthesis of Compound 1-7

LiOH (750 mg, 17.9 mmol, 2.0 equivalent) was added to the mixed solution of compound 1-6 (5.01 g, 9.02 mmol) in MeOH (40 ml), H₂O (10 ml) and THF (10 ml) at 0° C. Benzene was added to the reaction solution and concentrated by vacuum. 10% of aqueous solution of citric acid was added to the residue and extracted by EtOAc. Organic layer was washed by brine and dried by MgSO₄ and concentrated by vacuum. Thus the compound 1-7 (4.90 g, 9.05 mmol, 100%) was obtained as a white solid. The physical property of the compound 1-7 is shown in Tale 15.

TABLE 15

| Compound 1-7 |
|---|
| $[\alpha]D^{27}$ -14.1° (c = 5.00, CHCl₃); IR (neat film) 3309, 2560, 1716, 1497, 1471, 1404, 1368, 1307, 1243, 1163, 1063, 1008, 907, 845, 804 cm⁻¹; 1H NMR (400 MHz, CDCl₃) δ 7.61 (br, 2H), 7.36-7.44 (br, 3H), 6.90 (s, 1H), 5.00 (br, 2H), 4.63 (br, 1H), 3.83 (s, 3H), 3.43 (br, 1H), 2.94-3.20 (br, 1H), 2.25 (s, 3H), 1.10-1.40 (br, 9H); ¹³C NMR (100 MHz, CDCl₃) δ 176.2, 175.4, 156.7, 155.2, 151.4, 150.4, 150.3, 136.9, 135.8, 135.3, 132.3, 132.2, 128.7, 128.6, 128.4, 128.4, 128.1, 127.9, 97.1, 96.7, 81.1, 80.1, 77.2, 74.5, 60.4, 60.3, 54.1, 53.8, 53.7, 44.6, 42.3, 42.2, 42.2, 28.2, 27.9, 15.6. |

Example 3

The processes for synthesis of the compound 3-6 contained in general formula 3 and whole products in each process are shown in following synthetic process C.

Synthetic Process C

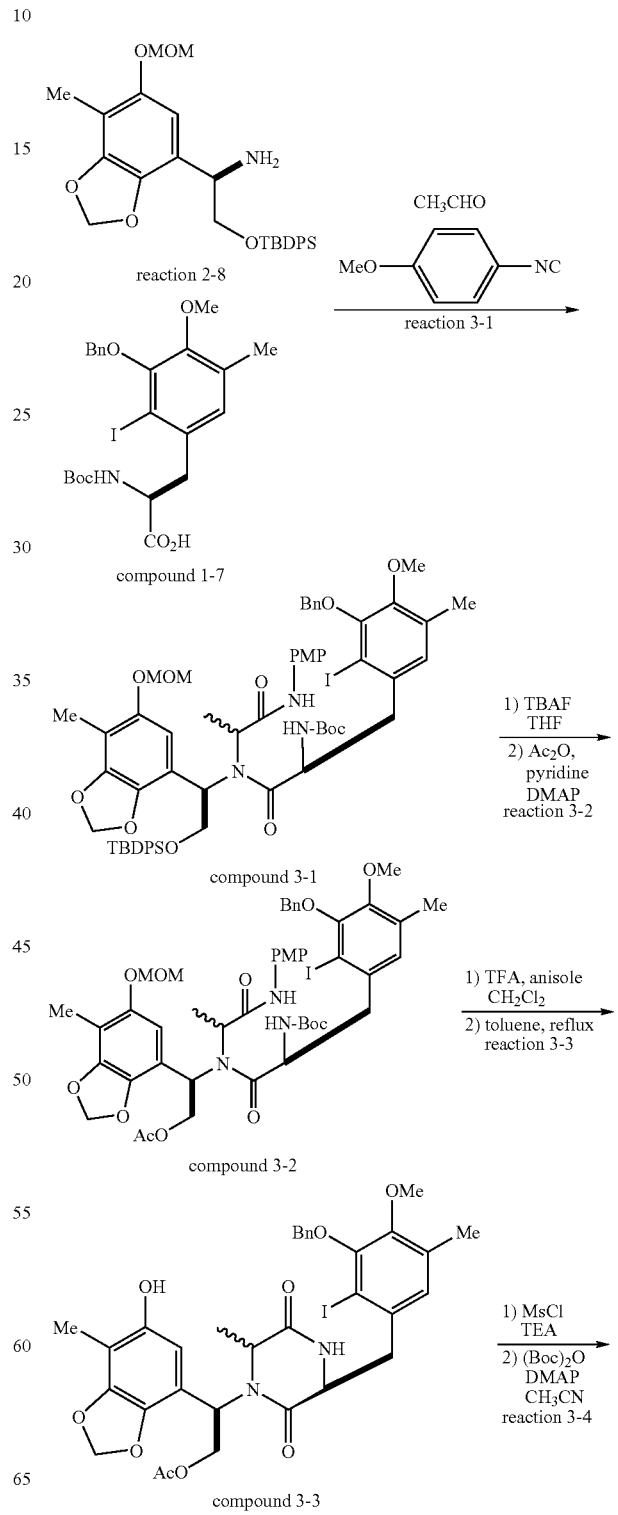

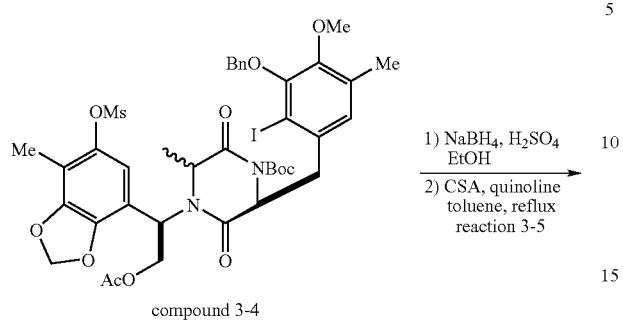

compound 3-4

1) NaBH₄, H₂SO₄ EtOH
2) CSA, quinoline toluene, reflux
reaction 3-5

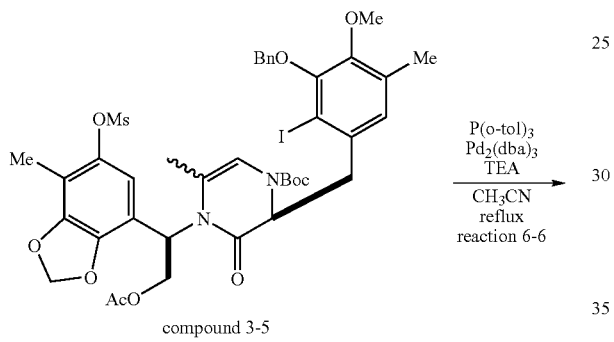

compound 3-5

P(o-tol)₃
Pd₂(dba)₃
TEA
CH₃CN
reflux
reaction 6-6

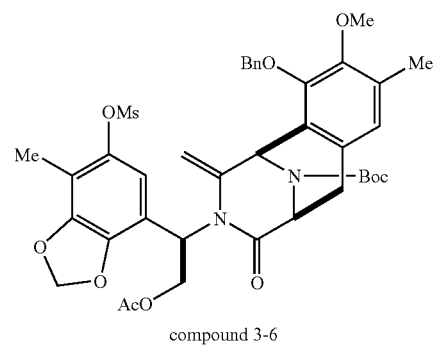

compound 3-6

Detail of Synthesis of C;

Synthesis of Compound 3-1

To the MeOH solution (200 ml) of compound 2-8 (9.63 g, 19.5 mmol), compound 1-7 (10.57 g, 19.5 mmol) and p-methoxyphenylisocyanide (3.90 g, 29.3 mmol, 1.5 equivalent), acetoaldehyde (22 ml, 0.39 mol, 20 equivalent) was added at room temperature and refluxed for 1 hour. After concentrated by vacuum, residue was purified by silica gel chromatography (40% EtOAc, n-hexane) and compound 3-1 (21.02 g, 17.6 mmol, 90%) was obtained as a yellow solid. The physical properties of 3-1 are shown in Table 16.

TABLE 16

| Compound 3-1 |
|---|
| IR (neat film) 3315, 1699, 1687, 1511, 1463, 1428, 1367, 1245, 1159, 1112, 1062, 826 cm$^{-1}$; $^1$H NMR (400 MHz, CDCl$_3$) δ 8.60-9.20 (m, 1H), 7.25-7.75 (m, 17H), 6.50-7.20 (m, 4H), 4.80-5.85 (m, 9H), 3.90-4.80 (m, 3H), 3.60-3.85 (m, 6H), 3.40-3.50 (m, 3H), 2.90-3.50 (m, 2H), 1.85-2.25 (m, 6H), 0.75-1.50 (m, 21H); $^{13}$C NMR (100 MHz, CDCl$_3$) δ 173.4, 172.0, 171.3, 170.1, 168.7, 167.9, 156.2, 156.1, 155.9, 155.6, 155.3, 154.3, 151.5, 151.4, 151.3, 151.0, 150.9, 150.8, 150.5, 150.1, 150.0, 146.9, 146.5, 139.8, 139.7, 136.8, 136.7, 136.6, 136.5, 135.6, 135.5, 135.4, 135.3, 135.2, 132.6, 132.5, 132.4, 132.2, 132.1, 132.0, 131.6, 131.1, 131.0, 129.9, 129.7, 129.6, 129.3, 128.5, 128.4, 128.3, 128.2, 128.0, 127.9, 127.7, 127.5, 127.4, 127.3, 123.0, 121.7, 121.5, 120.5, 113.7, 113.5, 113.4, 113.3, 113.1, 110.9, 106.2, 106.0, 100.9, 100.6, 97.5, 96.7, 96.6, 96.2, 95.8, 95.5, 95.3, 80.6, 80.5, 80.3, 79.3, 79.0, 74.4, 74.3, 71.5, 70.4, 62.6, 62.5, 60.2, 60.1, 59.7, 57.2, 56.2, 56.1, 55.9, 55.1, 54.5, 54.4, 51.5, 51.3, 42.9, 41.8, 41.1, 41.1, 28.1, 28.0, 27.9, 27.8, 27.1, 27.0, 26.9, 26.4, 19.1, 19.0, 18.9, 17.8, 17.1, 15.4, 15.3, 15.2, 15.1, 14.9, 14.8, 8.8 8.7, 8.5; |

Synthesis of Compound 3-2

TBAF (1M THF solution, 20 ml, 20.0 mmol) was added to THF solution (200 ml) of compound 3-1 (21.02 g, 17.6 mmol) was added at room temperature and stirred for 30 minutes. The mixed solvent of EtOH and n-hexane (3:7) was added and concentrated by vacuum. The residue was purified by silica gel chromatography (EtOAc) and yellow solid (14.90 g, 15.6 mmol, 89%) was obtained DMPA (97 mg, 0.79 mmol) was added to the mixed solution of acetic anhydride (30 ml) of alcohol (14.90 g, 15.6 mmol) and pyridine (60 ml) and stirred for 30 minutes at 50° C. After concentrated by vacuum, residue was purified by silica gel chromatography (60%, EtOAc n-hexane) and the compound 3-2 (14.54 g, 14.6 mmol, 93%) was obtained as yellow solid. The physical properties of compound 3-2 are shown in Table 17.

Synthesis of Compound 3-3

To the $CH_2Cl_2$ (290 ml) solution of compound 3-2 (14.5 g, 14.5 mmol) and anisole (79 ml, 0.73 mol), TFA (58 ml, 0.75 mol) was added at 0° C., then stirred at room temperature for 9 hours. 7% $Na_2SO_4$ aqueous solution was added to the reaction solution and extracted by EtOAc. The organic layer was washed by saturated aqueous solution of $NaHCO_3$ and by brine, dried by $MgSO_4$ and concentrated to 300 ml, then heat refluxed for 1 hour. The solvent was evaporated off by vacuum, and the residue was purified by column chromatography (in 70% EtOAc m-hexane). Thus the compound 3-3 (19.7 g, 27.0 mmol, 87%) was obtained as a brownish powder. The physical property of the compound 3-3 is shown in Table 18.

TABLE 17

| Compound 3-2 |
| --- |
| IR (neat film) 3318, 1743, 1700, 1511, 1436, 1368, 1304, 1245, 1170, 1112, 1060, 830 $cm^{-1}$; $^1H$ NMR (400 MHz, $CDCl_3$) δ 8.90-9.30 (m, 1H), 7.55 (d, J = 6.8 Hz, 2H), 7.20-7.50 (m, 5H), 6.30-7.20 (m, 2H), 6.80 (d, J = 6.8 Hz, 2H), 5.84-5.88 (br, 2H), 5.60-5.80 (m, 2H), 5.20-5.45 (m, 2H), 5.00-5.20 (m, 2H), 4.93-4.97 (m, 2H), 4.70-4.90 (m, 1H), 4.40-4.70 (m, 1H), 3.65-3.80 (m, 6H), 3.35-3.50 (m, 3H), 2.90-3.35 M, 1H), 1.80-2.25 (m, 9H), 1.10-1.55 (m, 12H); $^{13}C$ NMR (100 MHz, $CDCl_3$) δ 173.6, 173.2, 172.7, 172.0, 170.1, 170.0, 169.7, 169.5, 169.5, 169.4, 168.2, 156.4, 156.1, 155.8, 155.2, 154.3, 151.5, 151.3, 151.2, 151.2, 151.1, 150.6, 150.3, 147.1, 146.8, 146.6, 140.0, 139.8, 139.3, 136.8, 136.7, 136.7, 136.5, 135.0, 134.9, 134.6, 132.5, 132.0, 131.1, 131.0, 128.8, 128.5, 128.4, 128.4, 128.3, 128.2, 128.1, 128.0, 127.9, 121.8, 121.8, 121.8, 121.6, 121.4, 121.2, 120.6, 113.9, 113.9, 113.8, 113.5, 113.1, 112.6, 112.1, 111.7, 111.3, 105.9, 105.7, 105.3, 101.1, 101.0, 100.7, 96.8, 96.5, 95.4, 95.1, 79.6, 79.1, 74.4, 70.6, 62.0, 60.3, 60.2, 57.3, 56.5, 56.2, 56.0, 55.8, 55.2, 50.6, 50.1, 43.5, 28.1, 28.0, 27.9, 27.8, 20.9, 20.7, 17.6, 15.3, 14.8, 8.8; |

TABLE 18

| Compound 3-3 |
| --- |
| minor isomer; IR (neat film) 3345, 1752, 1683, 1652, 1456, 1306, 1232, 1093, 1037, 1007 $cm^{-1}$; $^1H$ NMR (400 MHz, $CDCl_3$) δ 7.56 (d, J = 8.2, 2H), 7.38-7.41 (m, 3H), 6.85 (s, 1H), 6.23 (s, 1H), 6.20 (br, 1H), 5.89 (s, 1H), 5.86 (s, 1H), 5.70 (dd, J = 8.4, 7.2 Hz, 1H), 4.95 (s, 2H), 4.69 (dd, J = 11.0, 7.2 Hz, 1H), 4.57 (dd, J = 11.0, 8.4 Hz, 1H), 4.29 (dd, J = 9.3, 3.9 Hz, 1H), 3.88 (q, J = 7.1 Hz, 1H), 3.80 (s, 3H), 3.46 (dd, J = 13.7, 3.9 Hz, 1H), 3.21 (dd, J = 13.7, 9.3 Hz, 1H), 2.21 (s, 3H), 2.09 (s, 3H), 2.05 (s, 3H), 1.45 (d, J = 7.1 Hz, 3H); $^{13}C$ NMR (100 MHz, $CDCl_3$) δ 170.7, 168.7, 166.5, 151.8, 15.0, 151.0, 147.0, 139.0, 136.7, 134.5, 133.2, 128.6, 128.4, 128.2, 128.1, 111.8, 109.1, 106.3, 100.9, 97.3, 74.6, 62.7, 60.4, 57.0, 55.0, 44.9, 21.2, 20.8, 15.5, 8.7; major isomer; IR (neat film) 3374, 1751, 1683, 1651, 1430, 1314, 1265, 1233, 1094, 1040, 1006 $cm^{-1}$; $^1H$ NMR (400 MHz, $CDCl_3$) δ (d, J = 8.3 Hz, 2H), 7.36-7.43 (m, 3H), 6.86 (s, 1H), 6.40 (s, 1H), 5.93 (2, 1H), 5.92 (s, 1H), 5.62 (dd, J = 8.9, 5.8 Hz, 1H), 5.50 (s, 1H), 5.15 (br, 1H), 5.03 (d, J = 6.8 Hz, 1H), 5.021 (d, J = 6.8 Hz, 1H), 4.76 (dd, J = 11.7, 8.9 Hz, 1H), 4.60 (dd, 11.7, 5.8 Hz, 1H), 4.34 (dd, J = 10.7, 3.9 Hz, 1H), 4.18 (q, J = 7.1 Hz, 1H), 3.84 (s, 3H), 3.81 (dd, J = 14.2, 3.9 Hz, 1H), 2.84 (dd, J = 14.2, 10.7 Hz, 1H), 2.25 (s, 3H), 2.13 (s, 3H), 2.07 (s, 3H), 1.15 (d, J = 7.1 Hz, 1H); $^{13}C$ MHz, $CDCl_3$) δ 170.7, 170.3, 166.9, 152.2, 151.0, 150.8, 146.8, 138.9, 136.6, 134.1, 133.4, 128.6, 128.4, 128.3, 128.2, 112.5, 108.9, 106.5, 101.0, 96.2, 74.6, 62.0, 60.4, 54.9, 53.3, 52.5, 41.5, 20.8, 18.0, 15.6, 8.7; |

Synthesis of Compound 3-4

To the CH$_2$Cl$_2$ (100 ml) solution of compound 3-3 (19.3 g, 26.4 mmol) and trimethylamine (11.8 ml, 84.6 mmol), MsCl (2.60 ml, 33.8 mmol) was added at 0° C., then stirred for 1 hour. EtOAc (400 ml) was added to the reaction solution and washed by 1N HCl, saturated NaHCO$_3$ aqueous solution and brine, then dried by MgSO$_4$. After concentrated by vacuum, the residue was purified by silica gel chromatography (in 70% EtOAc m-hexane). Thus, the mecyl body (19.4 g, 24.0 mmol, 91%) was obtained as a yellow solid. To the CH$_3$CN (15 ml) solution of mecyl body (3.00 g, 3.71 mmol) and (Boc)$_2$O (1.36 g, 6.22 mmol) was added and stirred for 6.5 hours. EtOAc was added to the reaction solution and washed with 0.5N HCl, saturated NaHCO$_3$ aqueous solution and brine. The organic layer was dried by MgSO$_4$, concentrated by vacuum and the residue was purified by silica gel chromatography (in 50% EtOAc n-hexane). Thus the compound 3-4 (3.27 g, 3.60 mmol, 97%) was obtained as a yellow solid. The physical property of the compound 3-4 is shown in Table 19.

TABLE 19

| Compound 3-4 |
|---|
| major isomer; IR (neat film) 1775, 1733, 1670, 1455, 1429, 1368, 1308, 1285, 1244, 1172, 1148, 1066, 970, 937 cm$^{-1}$; $^1$H NMR (400 MHz, CDCl$_3$) δ 7.58 (d, J = 6.8 Hz, 2H), 7.33-7.41 (m, 3H), 6.87 (s, 1H), 6.82 (s, 1H), 5.97 (s, 1H), 5.96 (s, 1H), 5.56, (dd, J = 8.0, 8.0 Hz, 1H), 5.14 (dd, J = 8.0, 4.8 Hz, 1H), 4.95 (d, J = 10.0 Hz, 1H), 4.91 (d, J = 10.0 Hz, 1H), 4.63 (dd, J = 10.8, 8.0 Hz, 1H), 4.56 (dd, J = 10.8, 8.0 Hz, 1H), 3.98 (q, J = 8.0, 1H), 3.78 (s, 3H), 3.53 (dd, J = 14.8, 4.8 Hz, 1H), 3.23 (dd, J = 14.8, 8.0 Hz, 1H), 3.16 (s, 3H), 2.20 (s, 3H), 2.19 (s, 3H), 2.03 (s, 3H), 1.45 (d, J = 8.0 Hz, 3H); $^{13}$C NMR (100 MHz, CDCl$_3$) δ 170.5, 167.8, 166.0, 151.8, 150.9, 149.5, 147.3, 144.1, 142.5, 136.8, 134.9, 132.9, 128.7, 128.4, 128.4, 128.2, 115.3, 115.1, 113.1, 102.1, 97.5, 84.4, 74.6, 62.0, 60.4, 59.5, 56.5, 56.5, 53.5, 44.6, 38.0, 27.8, 20.8, 20.8, 15.5, 9.9 |

Synthesis of Compound 3-5

To the EtOH (100 ml) and CH$_2$Cl$_2$ (10 ml) mixed solution of the compound 3-4 (4.11 g, 4.52 mmol), H$_2$SO$_4$ (3.0 ml, 9.0 mmol in 3.0M EtOH solution) and NaBH$_4$ (867 mg, 22.9 mmol) were added at 0° C. After acetone (10 ml) was added, neutralized by saturated NaHCO$_3$ aqueous solution, added EtOAc and filtrated by Cellite. Then concentrated by vacuum, EtOH was added to the residue and washed by saturated NaHCO$_3$ aqueous solution. The organic layer was dried by MgSO$_4$, concentrated by vacuum and aminal (4.19 g) was obtained. The obtained aminal is dissolved in toluene (40 ml), CSA (1.07 g, 4.61 mmol) and quinoline (0.82 ml, 7.0 mmol) are added and heat refluxed for 3 hours. EtOAc is added to the reaction solution and washed by 1N HCl aqueous solution, saturated NaHCO$_3$ aqueous solution and brine aqueous solution. The organic layer is dried by MgSO$_4$, concentrated by vacuum and the residue was purified by silica gel chromatography (in 50% EtOAc n-hexane). Thus the compound 3-5 (3.54 g, 3.97 mmol, 88%) was obtained as a yellow solid. The physical property of the compound 3-5 is shown in Table 20.

TABLE 20

| Compound 3-5 |
|---|
| [α]$_D^{27}$ +2.9° (c = 2.97, CHCl$_3$); IR (neat film) 1742, 1692, 1463, 1418, 1362, 1336, 1240, 1172, 1065, 1005, 962, 890, 805 cm$^{-1}$; $^1$H NMR (400 MHz, CDCl$_3$) δ 7.60 (d, J = 6.8 Hz, 2H), 7.36-7.44 (m, 3H), 6.87 (br, 1H), 6.69 (s, 1H), 6.21 (s, 1H), 6.01 (s, 1H), 5.96 (s, 1H), 4.97 (s, 2H), 4.93 (br, 1H), 4.85 (br, 2H), 3.80 (s, 3H), 3.19 (s, 3H), 2.91 (br, 2H), 2.22 (s, 3H), 2.20 (s, 3H), 2.04 (s, 3H), 1.32 (s, 9H); $^{13}$C NMR (100 MHz, CDCl$_3$) δ 170.3, 151.5, 151.3, 151.1, 150.9, 150.1, 150.1, 150.1, 146.7, 143.1, 143.0, 142.2, 142.1, 136.7, 136.6, 135.8, 134.7, 134.7, 132.0, 131.5, 129.2, 129.1, 128.4, 128.2, 127.9, 127.9, 127.9, 127.7, 126.2, 121.3, 120.8, 115.4, 115.2, 114.0, 113.9, 101.7, 97.0, 96.5, 80.8, 80.7, 77.3, 77.2, 77.0, 76.7, 74.2, 62.4, 62.3, 60.1, 60.0, 57.2, 55.7, 39.1, 38.8, 37.4, 37.4, 27.8, 27.5, 20.4, 16.3, 15.2, 9.6; |

Synthesis of Compound 3-6

Pd$_2$(dba)$_3$ (325 mg, 0.36 mmol, 5 mol %) was added to CH$_3$CN (50 ml) solution of the compound 3-5 (6.27 g, 7.02 mmol), P(o-tol)$_3$ (428 mg, 1.41 mmol, 0.2 equivalent) and triethylamine (4.0 ml, 29 mmol, 4.1 equivalent) and refluxed by heating for 2 hours. After EtOAc was added to the reaction solution and concentrated, EtOAc is added to the residue and washed by 10% citric acid, saturated NaHCO$_3$ aqueous solution and brine. The organic layer was dried by MgSO$_4$, concentrated by vacuum and the residue was purified by silica gel chromatography (in 50% EtOAc n-hexane). Thus the compound 3-6 (4.44 g, 5.81 mmol, 83%) was obtained as a yellow solid. The physical property of the compound 3-6 is shown in Table 21.

TABLE 21

Compound 3-6

[α]D$^{27}$ +38.4° (c = 1.85, CHCl$_3$); IR (neat film) 1743, 1699, 1636, 1424, 1367, 1309, 1233, 1173, 1113, 1065, 861, 808 cm$^{-1}$; $^1$H NMR (400 MHz, CDCl$_3$) δ 7.26-7.70 (m, 5H), 6.60-6.75 (br, 1H), 6.30-6.50 (br, 1H), 5.65-6.20 (br, 3H), 4.20-5.30 (br, 8H), 3.80 (s, 3H), 3.09 (s, 3H), 2.90-3.30 (br, 2H), 2.24 (s, 3H), 2.15 (s, 3H), 1.68 (s, 3H), 1.46 (s, 9H); $^{13}$C NMR (100 MHz, CDCl$_3$) δ 170.4, 149.7, 148.8, 147.0, 142.9, 142.6, 137.6, 132.3, 128.5, 127.8, 125.7, 115.2, 115.2, 114.0, 113.2, 113.1, 113.0, 113.0, 112.9, 101.8, 96.3, 95.4, 81.1, 74.1, 73.3, 60.3, 60.2, 59.9, 54.0, 54.0, 52.6, 50.5, 37.5, 31.9, 28.3, 20.1, 15.7, 9.9

Example 4

Processes and all products in each process in synthesis of the compound 4-8 contained in general formula 2 are shown in following synthesis process D.

Synthetic Process D

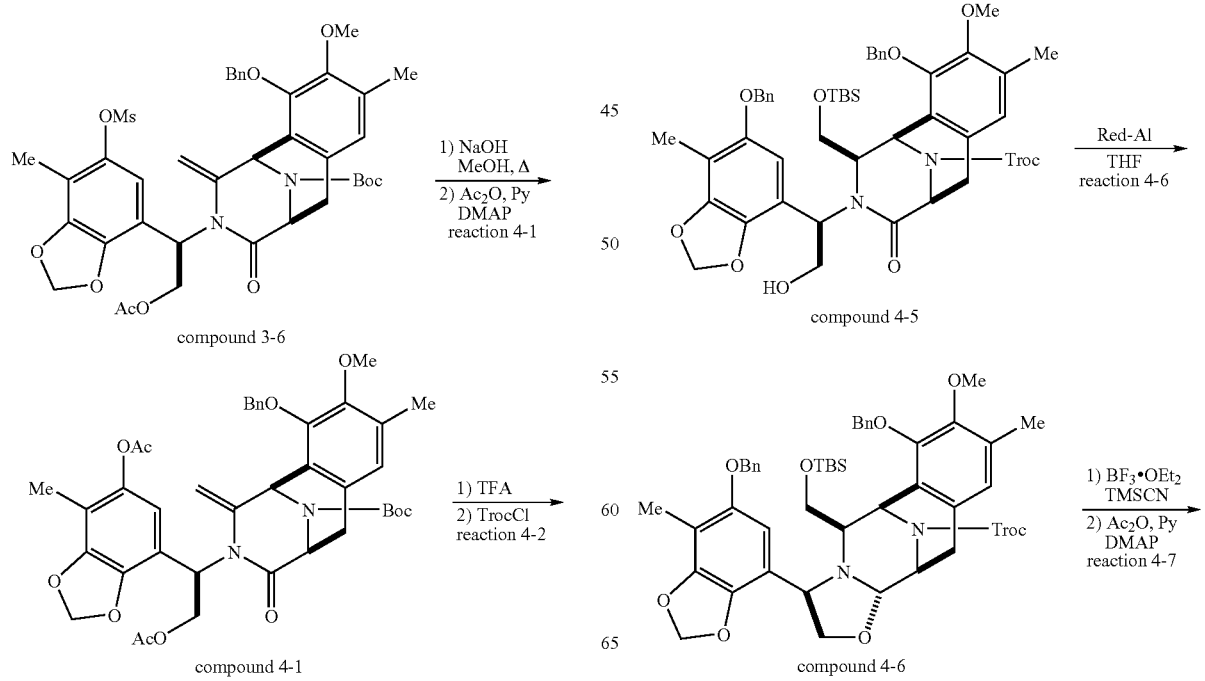

-continued

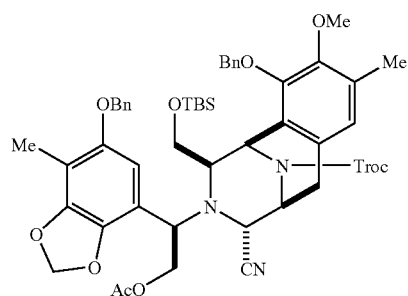

compound 4-7

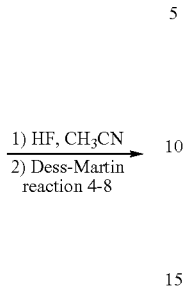

1) HF, CH₃CN
2) Dess-Martin
reaction 4-8

-continued

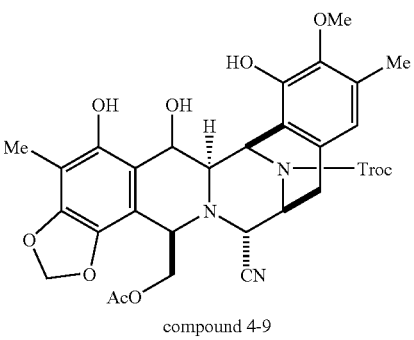

compound 4-9

Detail of Synthesis of D

Synthesis of Compound 4-1

2N NaOH aqueous solution (0.5 ml, 1 mmol) was added to MeOH solution (1.5 ml) of the compound 3-6 (120 mg, 0.157 mmol) was added and refluxed by heating for 2.5 hours. Et₂O and water were added to the reaction solution and acidificated by 1N HCl aqueous solution, then extracted by EtOAc. The organic layer was washed by saturated NaHCO₃ aqueous solution and brine and concentrated by vacuum. To the residue, pyridine (0.26 ml, 3.2 mmol) acetic acid anhydride (0.15 ml, 1.6 mmol) and DMPA (1 mg, 0.008 mmol) were added at room temperature. After concentrated by vacuum, the residue was purified by silica gel chromatography (in 30% EtOAc n-hexane). Thus the compound 4-1 (106 mg, 0.145 mmol, 93%) was obtained as a white solid. The physical property of the compound 4-1 is shown in Table 22.

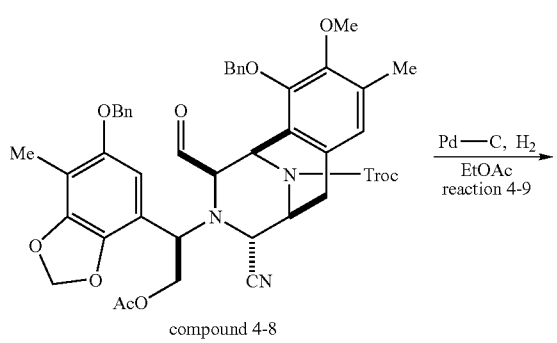

compound 4-8

Pd—C, H₂
EtOAc
reaction 4-9

TABLE 22

| Compound 4-1 |
|---|
| $[\alpha]_D^{26}$ +46.6° (c = 1.27, CHCl₃); IR (neat film) 1766, 1746, 1699, 1634, 1484, 1427, 1368, 1307, 1208, 1183, 1109, 1081, 937, 913, 862; ¹H NMR (40 MHz, CDCl₃) δ 7.26,-7.42 (m, 5H), 6.64 (br, 1H), 6.13 (br, 1H), 5.70-5.95 (br, 3H), 4.15-5.30 (br, 8H), 3.73 (s, 3H), 2.90-3.20 (br, 2H), 2.19 (s, 3H), 2.17 (s, 3H), 1.89 (s, 3H), 1.51 (s, 3H), 1.39 (s, 9H); ¹³C NMR (100 MHz, CDCl₃) δ 170.4, 169.2, 169.1, 149.8, 149.7, 149.7, 148.8, 146.8, 146.7, 144.3, 141.8, 140.4, 137.6, 137.6, 132.1, 132.1, 128.6, 128.5, 128.0, 128.0, 128.0, 127.9, 127.8, 127.7, 127.7, 127.7, 127.6, 127.5, 127.5, 127.5, 127.5, 125.7, 125.7, 125.7, 125.7, 115.3, 115.2, 115.2, 115.2, 115.2, 112.6, 112.2, 112.2, 112.2, 112.2, 101.6, 101.5, 81.0, 81.0, 81.0, 74.1, 74.1, 74.1, 73.6, 60.2, 59.6, 54.0, 52.8, 52.7, 52.7, 52.5, 52.5, 50.8, 50.7, 50.7, 50.7, 32.0, 28.3, 20.6, 20.6, 20.0, 15.7, 9.3; |

Synthesis of Compound 4-2

To the $CH_2Cl_2$ (12 ml) solution of the compound 4-1 (2.56 g, 3.51 mmol), TFA (3.0 ml, 39 mmol) was added at room temperature and stirred for 4 hours. The reaction solution was poured into saturated $NaHCO_3$ aqueous solution and extracted by $CH_2Cl_2$. After organic layer was concentrated by vacuum, the residue is dissolved in $CH_2Cl_2$ (12 ml) and saturated $NaHCO_3$ aqueous solution (20 ml) was added. To the reaction solution, TrocCl (0.47 ml, 3.5 mmol) was added and stirred for 10 minutes. The organic layer is dried by $MgSO_4$ and concentrated by vacuum. The residue was purified by silica gel chromatography (in 40% EtOAc n-hexane). Thus the compound 4-2 (2.08 g, 2.59 mmol, 1.74%) is obtained as a white powder. The physical property of the compound 4-2 is shown in Table 23.

TABLE 23

| Compound 4-2 |
| --- |
| $[\alpha]D^{26}$ +39.5 39.5 (c = 1.07, $CHCl_3$); IR (neat film) 1763, 1724, 1684, 1636, 1486, 1429, 1368, 1353, 1298, 1222, 1209, 1184, 1124, 1078, 1031 ,913, 863; $^1$H NMR (400 MHz, $CDCl_3$) δ 7.31-7.50 (m 5H), 6.74 (s, 1H), 6.22 & 6.20 (s, 1H), 6.00 & 5.96 (s, 1H), 5.87 & 5.77 (s, 2H), 6.72 & 4.50-5.25 (m, 9H), 4.37 & 4.29 (s, 1H), 3.79 (s, 3H), 3.10-3.30 (m 2H), 2.25 (s, 3H), 2.24 (s, 3H), 1.95 (s, 3H), 1.55 (s, 3H); $^{13}$C NMR (100 MHz, $CDCl_3$) δ 170.3, 169.2, 149.8, 144.3, 141.8, 137.4, 132.5, 128.5, 128.5, 127.9, 127.8, 127.6, 125.7, 124.8, 115.0, 112.5, 112.2, 101.5, 95.1, 75.0, 74.0, 73.8, 60.2, 53.9, 53.3, 52.5, 32.2, 31.8, 20.6, 19.9, 15.7, 9.2; |

Synthesis of Compound 4-3

To the MeOH (15.0 ml) solution of the compound 4-2 (681 mg, 0.847 mmol) dimethyloxilan (0.1M acetone solution, 15 ml, 1.5 mmol) was added at 0° C. and stirred for 2 hours. To the reaction solution, $Na_2SO_4$ (10 g) was added and stirred for 10 minutes, then CSA (7.2 mg, 0.03 mmol) was added and the temperature is elevated to room temperature. To the reaction solution, pyridine (25 μl, 0.31 mmol) was added so as to neutralize, then filtrated and concentrated by vacuum. The residue was purified by silica gel chromatography (in 50% EtOAc n-hexane) and the methoxy compound was obtained as a yellow powder.

THF solution (0.80 ml) of methoxy compound was added into TFA solution (4.0 ml) of $NaBH_3CN$ (160 mg, 2.54 mmol) at 0° C. and stirred for 40 minutes. $CHCl_3$ was added to the reaction solution and neutralized by saturated $NaHCO_3$ aqueous solution. The residue was passed through a column of basic alumina by EtOAc, then concentrated by vacuum. The residue was purified by silica gel chromatography (in 50% EtOAc n-hexane). Thus the compound 4-3 (150 mg, 0.182 mmol, 7.4%) was obtained as a white powder. The physical property of the compound 4-3 is shown in Table 24.

TABLE 24

| Compound 4-3 |
| --- |
| $[\alpha]D^{22}$ +33.2 (c = 1.23, $CHCl_3$); IR (neat film) 3510, 1764, 1722, 1664, 1484, 1428, 1369, 1342, 1304, 1227, 1185, 1126, 1062, 938, 911 cm$^{-1}$; IR NMR (400 MHz, CDCl3) δ 7.54 (d, J = 6.8 Hz, 2H), 7.38-7.48 (m, 3H), 6.83 & 6.80 (s, 1H), 6.36 & 6.33 (s, 1H), 5.78-5.87 (m, 3H), 5.40 (br, 1H), 5.26-5.30 (m, 1H), 5.11-5.16 (m 1H), 4.70-4.93 (m, 3H), 4.52 (br, 1H), 4.44 (m, 1H), 3.91 & 3.87 (s, 3H), 3.55-3.65 (br, 2H), 3.00-3.30 (m, 3H), 2.29 & 2.28 (s, 3H), 2.22 (s, 3H), 1.95 (s, 3H); $^{13}$C NMR (100 MHz, $CDCl_3$) δ 170.4, 170.3, 170.2, 169.8, 169.1, 152.0, 151.6, 149.4, 149.0, 148.5, 146.5, 146.4, 144.3, 144.2, 142.0, 142.0, 135.2, 135.2, 133.4, 133.2, 129.4, 129.2, 129.2, 129.1, 129.0, 129.0, 128.9, 127.3, 127.2, 122.3, 121.8, 113.7, 113.5, 113.1, 113.0, 101.7, 101.6, 95.2, 95.1, 77.2, 76.4, 75.2, 75.1, 62.7, 62.6, 6.5, 6.5, 59.5, 53.9, 53.2, 47.5, 46.9, 31.9, 31.6, 2.7, 2.6, 2.6, 15.7, 9.3; |

Synthesis of Compound 4-4

To the DMF solution (0.10 ml) of the compound 4-3 (101 mg, 0.123 mmol) and imidazole (21.3 mg, 0.313 mmol), TBSCl (28.0 mg, 0.186 mmol) was added at room temperature and stirred for 2 hours. The reaction solution was purified by silica gel chromatography (in 40% EtOAc n-hexane) and silanylether (106 mg, 0.127 mmol, 92%) was obtained as an oil. Silanylether (524 mg, 0.560 mmol) was dissolved in $G/GHNO_3$ solution (8.0 ml) and stirred for 2.5 hours at 40° C. EtOAc is added to the reaction solution and washed by 1N HCl aqueous solution, saturated $NaHCO_3$ aqueous solution and brine. The organic Layer was dried by $Na_2SO_4$ and concentrated by vacuum. The residue is purified by silica gel chromatography (in 50% EtOAc n-hexane). Thus the compound 4-4 (405 mg, 0.475 mmol, 85%) is obtained as a yellow powder. The physical property of the compound 4-4 is shown in Table 25.

TABLE 25

| Compound 4-4 |
| --- |
| $[\alpha]D^{23}$ −33.7° (c = 1.48, $CHCl_3$); IR (neat film) 3309, 1723, 1640, 1423, 1345, 1304, 1257, 1133, 1127, 1095, 838 cm$^{-1}$; $^1$H NMR (400 MHz, $CDCl_3$) δ 7.35-7.54 (m 5H), 6.87 & 6.83 (s, 1H), 6.30 (br, 1H), 5.35-5.73 (m 5H), 5.17-5.28 (m, 1H), 5.06-5.16 (m, 1H), 4.98 & 4.90 (d, J = 12.0 Hz, 1H), 4.60-4.86 (m, 3H), 4.27-4.40 (m, 3H), 4.08 (br, 1H), 3.80 & 3.74 (s, 3H), 3.15-3.35 (m, 3H), 2.28 (s, 3H), 1.94 & 1.91 (s, 3H), 0.69 & 0.68 (s, 9H), −0.27 & −0.30 (s, 3H), −0.32 & −0.35 (s, 3H); $^{13}$C NMR (100 MHz, $CDCl_3$) δ 151.9, 151.3, 150.1, 149.4, 148.7, 146.0, 136.6, 136.4, 133.2, 132.8, 129.2, 129.1, 128.7, 128.7, 128.6, 128.5, 128.4, 128.4, 126.5, 126.3, 123.2, 116.1, 106.3, 106.2, 105.0, 100.2, 95.0, 75.5, 75.3, 75.1, 68.3, 67.3, 63.1, 62.9, 62.0, 60.2, 58.7, 58.7, 53.6, 53.0, 48.8, 47.9, 32.2, 25.5, 17.8, 17.8, 15.6, 15.6, 8.4, 8.4, −5.9, −6.0, −6.1, −6.2 |

Synthesis of Compound 4-5

To the $CH_3CN$ (6.0 ml) solution of the compound 4-4 (404 mg, 0.474 mmol) and $K_2CO_3$ (196 mg, 1.42 mmol) BnBr (73.0 μl, 0.615 mmol) was added and refluxed by heat for 1 hour. $CHCl_3$ was added to the reaction solution and filtrated by Celite, then concentrated by vacuum. The residue was purified by silica gel chromatography (in 50% EtOAc n-hexane). Thus the compound 4-5 (409 mg, 0.434 mmol, 91%) was obtained as a yellow powder. The physical property of the compound 4-5 is shown in Table 26.

TABLE 26

Compound 4-5

[α]$D^{23}$ −37.4° (c = 2.11, CHCl$_3$); IR (neat film) 3749, 1717, 1419, 1340, 1253, 1111, 838 cm−1; 1H NMR (400 MHz, CDCl$_3$) δ 7.30-7.60 (m, 10H), 6.77 & 6.73 (s, 1H), 5.83 (s, 1H), 5.77 (br, 2H), 5.69 (s, 1H), 5.51 (br, 1H), 5.22 & 5.21 (d, J = 10.0 Hz, 1H), 5.14 (br, 1H), 5.00 & 4.88 (d, J = 11.6 Hz, 1H), 4.74 (d, J = 11.6 Hz, 1H), 4.68 (d, J = 10.0 Hz, 1H), 4.59 (d, J = 10.8 Hz, 1H), 4.50 & 4.46 (d, J = 11.6 Hz, 1H), 4.37 & 4.25, (br, 1H), 4.30 & 4.29 (d, J = 10.8 Hz, 1H), 4.05 & 3.95 (br, 2H), 3.80 & 3.75 (s, 3H), 3.13-3.37 (m, 3H), 1.99 & 1.96 (s, 9H), −0.27 & −0.32 (s, 3H), −0.33 & −0.36 (s, 3H); $^{13}$C NMR (100 MHz, CDCl$_3$) δ 170.2, 152.1, 152.1, 150.0, 148.8, 146.2, 137.2, 137.1, 136.5, 133.1, 129.2, 128.7, 128.6, 128.6, 128.5, 128.5, 128.0, 127.9, 127.8, 126.4, 126.3, 123.3, 115.8, 108.1, 102.6, 100.6, 75.5, 75.3, 75.2, 70.8, 67.5, 66.7, 63.5, 62.3, 60.3, 60.3, 59.8, 53.4, 52.7, 47.9, 47.2, 32.0, 31.5, 25.5, 22.6, 17.8, 15.5, 14.1, 8.7, −6.0, −6.3

Synthesis of Compound 4-6

To the THF solution (2.0 ml) of the compound 4-5 (224 mg, 0.238 mmol), Red-Al (1.3M toluene solution, 0.25 ml, 0.325 mmol) was added at 0° C. 1N HCl aqueous solution was added to the reaction solution and extracted by ETOAc. The organic layer was washed by saturated NaHCO$_3$ aqueous solution and brine, dried by MgSO$_4$ and concentrated by vacuum. The residue was purified by silica gel chromatography (in 30% EtOAc n-hexane). Thus the compound 4-6 (181 mg, 0.195 mmol, 82%) was obtained as a white solid. The physical property of the compound 4-6 is shown in Table 26.

TABLE 27

Compound 4-6

[α]$D^{22}$ −37.4° (c = 1.19, CHCl$_3$); IR (neat film) 1717, 1435, 1263, 1118, 1024, 840 cm$^{−1}$; $^1$H NMR (400 MHz, CDCl$_3$) δ 7.58 (d, J = 8.0 Hz, 1H), 7.50 (d, J = 6.8 Hz, 1H), 7.26-7.49 (m, 8H), 6.77 & 6.73 (s, 1H), 6.41 & 6.40 (s, 1H) 5.86 (s, 1H), 5.77 (s, 1H), 5.57 & 5.51 (s, 1H), 5.41 (br, 1H), 5.21 (dd, J = 10.4, 10.4 Hz, 1H), 4.93 (dd, J = 7.2, 6.0 Hz, 1H), 4.69-5.02 (m, 5H), 4.20-4.35 (m, 3H), 3.87 & 3.83 (s, 3H), 3.74 (m, 1H), 3.14-3.35 (m, 3H), 2.73 (dd, J = 17.6, 6.0 Hz, 1zh9, 2.21 (s, 3H), 2.09 (s, 3H), 0.71 & 0.69 (s, 9H), −0.21 & −0.26 (s, 3H), −0.27 & 0.31 (s, 3H); $^{13}$C NMR (100 MHz, CDCl$_3$) δ 153.1, 153.5, 151.8, 149.5, 149.4, 148.1, 147.6, 146.5, 138.2, 137.4, 137.3, 131.4, 131.2, 130.2, 129.9, 128.6, 128.5, 128.4, 128.3, 128.0, 127.9, 127.7, 127.2, 127.2, 125.5, 125.0, 124.4, 120.7, 120.6, 107.9, 101.9, 101.7, 100.7, 100.6, 95.4, 92.1, 92.1, 75.5, 75.2, 75.0, 74.8, 70.3, 68.9, 68.3, 68.1, 66.7, 60.5, 60.3, 60.2, 60.1, 60.0, 59.9, 48.5, 48.1, 47.5, 46.7, 30.7, 30.5, 25.6, 17.8, 15.7, 15.7, 8.7, −5.9, −5.9, −6.0, −6.0

Synthesis of Compound 4-7

To the CH$_2$Cl$_2$ (5.0 ml) solution of the compound 4-6 (2.95 g, 0.318 mmol) and TMSCN (127 μl, 0.952 mmol, 3.0 equivalent), BF$_3$.OEt$_2$ (in 1.0M CH$_2$Cl$_2$ solution, 480 μl, 0.48 mmol) was added at 0° C. The reaction solution was poured into saturated NaHCO$_3$ aqueous solution, extracted by CH$_2$Cl$_2$, and organic layer was dried by MgSO$_4$ then concentrated by vacuum. The residue was purified by silica gel chromatography (in 50% EtOAc n-hexane) and nitrile compound (221 mg, 0.232 mmol) was obtained as a white solid. To the reaction solution of nitrile compound (221 mg, 0.232 mmol), acetic anhydride (1.0 ml) and pyridine (2.0 ml), DMPA (5.6 mg, 0.05 mmol) was added and stirred for 1 hour at room temperature. After reaction solution is concentrated by vacuum, residue is purified by silica gel chromatography (in 30% EtOAc n-hexane) and the compound 4-7 (213 mg, 0.214 mg, 92%) was obtained as a white solid. Physical properties of the Compound 4-7 are shown in Table 28.

TABLE 28

Compound 4-7

[α]$D^{23}$ +49.9° (c = 1.82, CHCl$_3$); IR (neat film) 1720, 1430, 1251, 1122, 840 cm$^{−1}$; $^1$H NMR (400 MHz, CDCl$_3$) δ 7.26-7.65 (m, 10H), 6.52, 6.49 (s, 1H), 6.10 (br, 1H), 5.67 (s, 1H), 5.50 & 5.35 (s, 1H), 5.37 (s, 1H), 4.55-5.30 (m, 8H), 5.50-5.55 (m, 3H), 3.89 & 3.83 (s, 3H), 3.65-3.80 8br, 1H), 3.40-3.55 (br, 2H), 2.85 & 2.80 (dd, J = 17.6, 8.0 Hz, 1H), 2.20-2.30 (br, 6H), 1.90-2.00 (br, 3H), 1.53 & 1.65 (d, J = 17.0 Hz, 1H), 0.77 (br, 9H), −0.04 & 0.11 (s, 3H), −0.08 & −0.14 (s, 3H); $^{13}$C NMR (100 MHz, CDCl$_3$) δ 170.2, 170.1, 152.6, 152.2, 151.0, 150.8, 149.0, 148.9, 147.6, 147.0, 146.7, 139.7, 139.7, 137.6, 137.4, 137.2, 131.2, 130.9, 130.6, 128.6, 128.6, 128.5, 128.4, 128.1, 128.0, 127.8, 127.7, 127.1, 125.4, 124.9, 124.9, 124.8, 117.9, 1117.9, 117.8, 115.6, 115.6, 109.4, 109.3, 103.6, 103.5, 100.5, 95.2, 95.1, 75.6, 75.1, 74.8, 70.4, 70.2, 63.3, 63.1, 61.9, 61.2, 60.2, 59.3, 54.2, 54.0, 51.8, 51.6, 50.2, 49.3, 49.1, 48.7, 29.8, 29.7, 25.7, 20.8, 20.8, 18.1, 18.1, 15.5, 8.9, −5.7, −5.8, −6.0, −6.1;

Synthesis of Compound 4-8

To the CH$_3$CN (2.0 ml) solution of the compound 4-7 (200 mg, 0.20 mmol), HF (48 wt % aqueous solution, 1.0 ml, 28 mmol) was added and stirred for 3 hours. The reaction solution is poured into saturated NaHCO$_3$ aqueous solution and extracted by EtOAc. The organic layer was washed by brine and concentrated by vacuum. The residue was purified by silica gel chromatography (in 40% AcOEt n-hexane) and alcohol compound (180 mg, 0.20 mmol, 100%) was obtained as a white solid. To the CH$_2$Cl$_2$ (2.5 ml) solution of Dess-Martin reagent (103 mg, 0.243 mmol) was added at room temperature and stirred for 30 minutes. Reaction was stopped by adding 2-propanol (20 μL), then Et$_2$O was added, filtrated by Celite and concentrated by vacuum. The residue was dissolved in EtOAc and washed by saturated NaHCO$_3$ aqueous solution and brine. The organic layer was dried by MgSO$_4$ and concentrated by vacuum. The residue was purified by silica gel chromatography (in 40% EtOAc n-hexane) and the compound 4-8 (165 mg, 0.188 mmol, 92%) was obtained as a white solid. Dess-Martin reagent is shown by following chemical formula.

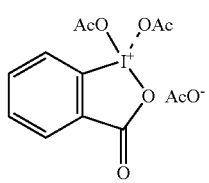

Physical properties of the Compound 4-7 are shown in Table 29.

TABLE 29

Compound 4-8

[α]$D^{24}$ +23.2° (c = 0.90, CHCl$_3$); IR (neat film) 1732, 1607, 1584, 1488, 1382, 1315, 1238, 1122, 1035, 939, 906, 826 cm$^{-1}$; $^1$H NMR (400 MHz, CDCl$_3$) δ 9.17 & 9.12 (d, 2.8H), 7.23-7.45 (m, 10H), 6.61 & 6.59 (s, 1H), 5.93 (br, 1H), 5.80 (br, 1H), 5.75 & 5.72 (br, 1H), 5.62 (br, 1H), 5.21 & 5.18 (d, J = 10.8 Hz, 1H), 4.65-5.00 (m, 8H), 4.27-4.52 (M, 3H), 3.78 & 3.71 (s, 3H), 3.68 (br, 1H), 3.13 & 3.08 (dd, J = 17.6, 8.0 Hz, 1H), 2.12 (br, 1H), 2.04-2.11 (br, 6H), 2.01 & 2.01 (s, 3H); $^{13}$C NMR (100 MHz, CDCl$_3$) δ 196.9, 196.4, 170.2, 152.4, 152.1, 146.7, 139.8, 137.1, 137.1, 132.0, 130.5, 128.6, 128.5, 128.4, 128.0, 127.9, 127.9, 127.8, 127.2, 127.2, 127.0, 125.0, 124.9, 123.9, 113.5, 113.4, 110.4, 103.9, 100.9, 95.0, 75.3, 74.4, 70.5, 70.4, 68.9, 68.4, 62.3, 60.5, 56.8, 51.8, 51.7, 50.1, 49.1, 47.2, 30.0, 20.9, 15.8, 9.0

Synthesis of Compound 4-8

THF (1.2 ml) solution of the compound 4-8 (51.2 mg, 0.058 mmol) and 10% Pd—C (51.1 mg, 0.024 mmol) was stirred for 18 hours at room temperature under the 1 atmospheric pressure of hydrogen gas. The reaction solution was filtrated by Cellite and concentrated by vacuum. The residue was purified by silica gel chromatography (in 50% EtOAc n-hexane) and the compound 4-9 (34.2 mg, 0.049 mmol, 84%) was obtained as a yellow film. Physical properties of the Compound 4-7 are shown in Table 30.

TABLE 30

Compound 4-9

[α]$D^{24}$ +23.1° (c = 1.37, CHCl$_3$); IR (neat film) 3749, 1722, 1623, 1587, 1501, 1435, 1380, 1317, 1265, 1232, 1127, 1105, 1056, 1032, 1012, 965 cm$^{-1}$; $^1$H NMR (400 MHz, CDCl$_3$) δ 6.55 (s, 1H), 5.92 (s, 1H), 5.85 & 5.80 (s, 1H), 5.83 8s, 1H), 4.91 & 4.87 (d, J = 8.0 Hz, 1H), 4.87 & 4.85 8d, J = 11.6 Hz, 1H), 4.69 & 4.67 (d, J = 11.6 Hz, 1H), 4.48 (d, 10.4 Hz, 1H), 4.46 (m, 1H), 4.19 (br, 1H), 4.07 (br, 1H), 3.77 & 3.76 (s, 3H), 3.66 (dd, J = 10.8, 8.0 Hz, 1H), 3.34 & 3.31 (dd, J = 10.4, 2.8 Hz, 1H), 3.25 (dd, J = 17.6, 8.0 Hz, 1H), 2.85 & 2.80 (d, J = 17.6 Hz, 1H), 2.25 & 2.24 (s, 3H); $^{13}$C NMR (100 MHz, CDCl$_3$) δ 170.3, 153.1, 152.5, 149.3, 149.2, 145.9, 145.9, 144.0, 143.7, 142.5, 142.3, 135.4, 135.3, 131.6, 131.3, 130.1, 130.1, 123.1, 122.9, 117.0, 116.9, 115.9, 115.8, 110.0, 109.9, 108.0, 101.0, 95.3, 95.0, 75.3, 75.1, 68.9, 68.8, 64.1, 61.6, 61.5, 61.1, 61.0, 58.9, 58.8, 56.3, 49.6, 48.9, 47.1, 46.4, 30.5, 29.6, 20.2, 15.7, 15.7, 8.6

Example 5

Synthesis of compounds contained in general formula 1. Each process from reaction 5-1 to reaction 5-3 and products from each process are shown in synthetic process E.

Synthetic Process E;

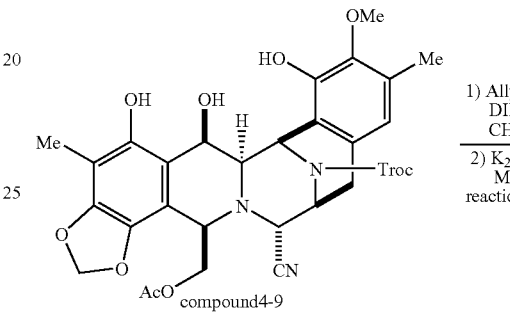
compound4-9

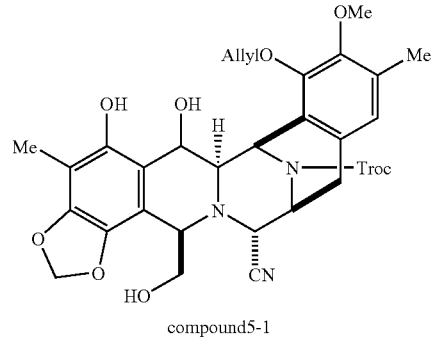
compound5-1

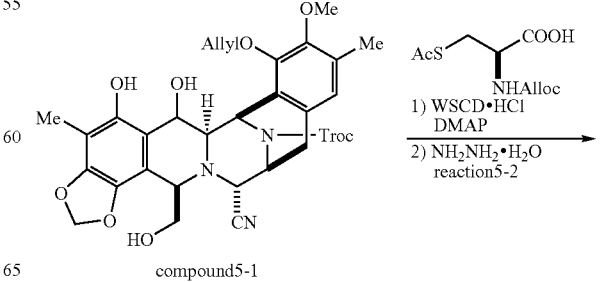
compound5-1

-continued

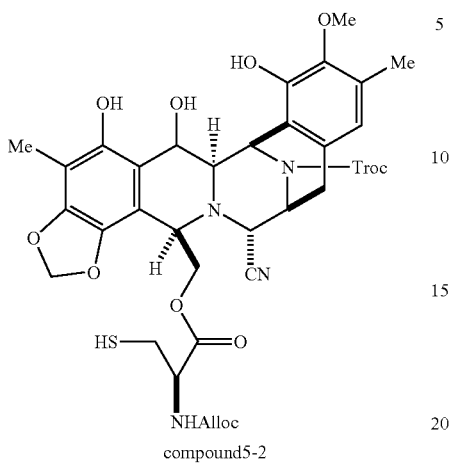
compound5-2

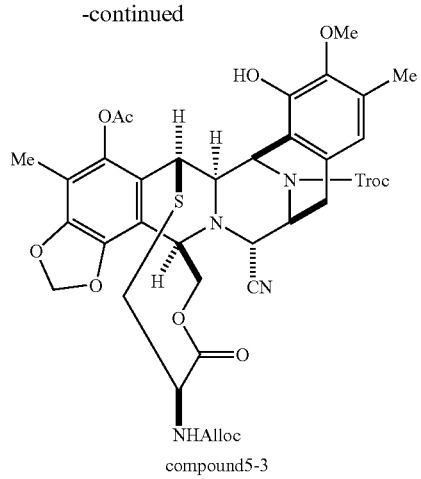
compound5-3

Details of Synthetic Process E

Synthesis of Compound 5-1

To the $CH_2Cl_2$ (1.2 ml) solution of the compound 4-9 (34.2 mg, 0.049 mmol) and i-$Pr_2$NEt (0.20 ml, 1.2 mmol), AllylBr (40 μl, 0.47 mmol) was added and heat refluxed for 3 hours. $CH_2Cl_2$ was added to the reaction solution, washed by 1N HCl aqueous solution, saturated $NaHCO_3$ aqueous solution and brine. The organic layer was dried by $MgSO_4$ and concentrated by vacuum. The residue was purified by silica gel chromatography (in 50% EtOAc n-hexane) and allylether (32.3 mg, 0.044 mmol, 89%) was obtained. To the MeOH (0.6 ml) solution of the allylether (32.3 mg, 0.044 mmol), $K_2CO_3$ (70.8 mg, 0.51 mmol) was added and stirred for 30 minutes at room temperature. EtOAc was added to the reaction solution, and washed by 10% citric acid, saturated $NaHCO_3$ aqueous solution and brine. The organic layer was washed by $MgSO_4$ and concentrated by vacuum. The residue was purified by silica gel chromatography (in 50% EtOAc n-hexane) and the compound 5-1 (30.3 mg, 0.044 mmol, 99%) was obtained as a colorless film. Physical properties of the Compound 5-1 are shown in Table 31.

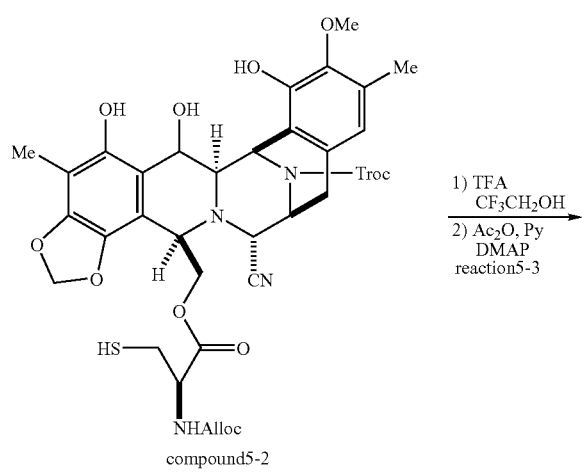
compound5-2

1) TFA
   $CF_3CH_2OH$
2) $Ac_2O$, Py
   DMAP
reaction5-3

TABLE 31

| Compound 5-1 |
|---|
| $[α]D^{26}$ +43.8° (c = 1.11, $CHCl_3$); IR (neat film) 3298, 1720, 1486, 1434, 1378, 1336, 1315, 1267, 1229, 1125, 1058, 1032, 965, 827 $cm^{-1}$; $^1H$ NMR (400 MHz, $CDCl_3$) δ 9.59 & 9.57 (s, 1H), 6.81 & 6.78 (s, 1H), 6.20 (m, 1H), 5.65-5.95 (m, 4H), 5.40-5.60 (m, 2H), 4.60-5.00 (m, 4H), 4.50 (m, 2H), 4.20-4.40 (m, 2H), 4.00 (m, 1H), 3.84 & 3.82 (s, 3H), 3.60 (m, 1H), 3.20-3.35 (m, 3H), 2.86 (d, J = 17.6 Hz, 1H), 2.24 & 2.23 (s, 3H), 2.06 & 2.04 (s, 3H); $^{13}C$ NMR (100 MHz, $CDCl_3$) δ 152.8, 152.2, 149.4, 149.3, 148.7, 147.4, 147.0, 145.8, 135.4, 135.3, 133.0, 132.7, 132.0, 130.5, 130.1, 126.5, 126.5, 123.8, 123.0, 121.7, 121.3, 115.7, 115.7, 110.2, 109.5, 109.4, 107.9, 100.9, 100.9, 95.1, 15.0, 77.2, 76.1, 75.6, 75.5, 75.2, 68.9, 68.7, 68.5, 65.5, 65.5, 62.0, 61.4, 60.6, 60.6, 59.3, 59.3, 58.3, 58.2, 49.8, 48.6, 47.4, 47.0, 30.7, 30.7, 30.6, 15.8; |

Synthesis of Compound 5-2

To the CH$_2$Cl$_2$ (1.60 ml) solution of the compound 5-1 (51.0 mg, 0.073 mmol) and S-acetyl-N-alloccystein (42.7 mg, 0.173 mmol), WSCD.HCl (37.2 mg, 0.194 mmol) and DMAP (1.9 mg, 0.008 mmol) were added at room temperature. After stirred for 10 minutes, CH$_2$Cl$_2$ was added to the reaction solution, and washed by 1N HCl aqueous solution, saturated NaHCO$_3$ aqueous solution and brine. The organic layer was concentrated by vacuum, and the residue was purified by silica gel chromatography (in 50% EtOAc n-hexane) and ester (64.0 mg, 0.070 mmol, 94%) was obtained as a yellow film.

To the CH$_3$CN (0.80 ml) solution of ester (29.5 mg, 0.032 mmol), hydrazine solution (upper layer of 1:3 mixture (by volume) of hydrazine hydride and CH$_3$CN$_3$, 35 μl) was added and stirred for 1.5 minutes at room temperature. CHCl$_3$ was added to the reaction solution, washed by 1N HCl aqueous solution, saturated NaHCO$_3$ aqueous solution and brine and dried by Na$_2$SO$_4$. Solution was evaporated off and the compound 5-2 (27.8 mg, 0.03 μmol, 98%) was obtained as a colorless film. Physical properties of the Compound 5-2 are shown in Table 32.

TABLE 32

| Compound 5-2 |
|---|
| [α]$_D^{24}$ +22.8° (c = 1.11, CHCl$_3$); IR (neat film) 3297, 1718, 1507, 1436, 1375, 1338, 1298, 1263, 1125, 1102, 1059, 1032, 1013, 968, 939, 827 cm$^{-1}$; $^1$H NMR (400 MHz, CDCl$_3$) δ 9.50-9.65 (m, 1H), 7.26-7.40 (m, 5H), 6.72-6.83 (m, 1H), 6.23 (m, 1H), 6.12 & 6.09 (d, J = 4.0 Hz, 1H), 5.95 (s, 1H), 5.88 (m, 1H), 5.81, (s, 1H), 5.79 & 5.69 (s, 1H) 5.20-5.60 (m, 4H), 4.77-5.02 (m, 3H), 4.63-4.72 (m, 1H), 4.27-4.64 (m, 4H), 4.08-4.27 (m, 3H), 3.95-4.68 (m, 1H), 3.87 (s, 3H), 3.89 (s, 3H), 3.15-3.35 (m, 2H), 2.70-3.05 (m, 1H), 2.88 8d, J = 17.6 Hz, 1H), 2.50-2.70 (m, 2H), 2.27 & 2.25 (s, 3H), 2.08 (s, 3H), 0.85-1.45 (m, 2H); $^{13}$C NMR (100 MHz, CDCl$_3$) δ 169.8, 169.5, 155.3, 152.8, 152.2, 149.6, 149.5, 148.6, 148.5, 147.5, 147.0, 145.9, 135.3, 132.7, 132.5, 132.4, 132.3, 132.0, 132.0, 131.0, 130.6, 126.7, 126.6, 123.9, 123.2, 121.7, 121.6, 121.1, 118.4, 118.2, 118.1, 115.6, 115.6, 110.0, 109.0, 109.2, 108.4, 108.2, 101.0, 95.2, 95.1, 76.2, 75.6, 75.6, 75.3, 68.9, 68.7, 68.6, 66.2, 66.1, 66.0, 65.1, 61.9, 61.4, 60.8, 60.7, 59.1, 58.8, 56.7, 55.2, 55.1, 54.8, 52.8, 49.7, 48.8, 47.1, 46.9, 46.8, 31.6, 30.5, 30.3, 30.1, 27.2, 26.8, 26.5, 22.6, 15.9, 15.8, 15.8, 14.2, 14.1, 8.6; |

Synthesis of Compound 5-3

To the trifluoroethanol solution of the compound 5-2 (24.6 mg, 0.028 mmol), TFA (10% 2,2,2-trifluoroethanol, 0.15 ml, 0.19 mmol) was added at room temperature and stirred for 3 hours. Benzene was added to the reaction solution and concentrated by vacuum. The obtained residue was dissolved in acetate anhydride (0.1 ml) and pyridine (0.2 ml), then DMAP (1.5 mg, 0.012 mmol) was added and stirred for 30 minutes. The reaction solution was concentrated by vacuum and the residue was purified in PTLC (30% EtOAc n-hexane). The compound 5-3 (18.0 mg, 0.020 mmol, 71%) was obtained as a colorless film. Physical properties of the Compound 5-3 are shown in Table 33.

TABLE 33

| Compound 5-3 |
|---|
| [α]$_D^{23}$ −22.2° (c = 1.06, CHCl$_3$); IR (neat film) 3402, 1759, 1721, 1510, 1431, 1372, 1332, 1309, 1265, 1236, 1193, 1125, 1101, 1-87, 1060, 1029, 1007, 983, 916, 826 cm$^{-1}$; $^1$H NMR (400 MHz, CDCl$_3$) δ 6.79 & 6.78 (s, 1H), 6.18 (m, 1H), 6.10 (s, 1H), 6.01 & 5.99 (s, 1H), 5.94 (m, 1H), 5.45-5.68 (m, 2H), 5.22-5.35 (m, 3H), 4.97-5.15 (m, 3H), 4.65-4.90 (m, 3H), 4.42-4.63 (m, 5H), 4.33 (br, 1H), 4.15-4.27 (m, 4H), 3.81 & 3.87 (s, 3H), 3.43 (s, 1H), 3.12-3.29 (m, 2H), 2.30-2.38 (m, 2H), 2.29 & 2.28 (s, 3H), 2.26 & 2.25 (s, 3H), 2.03 (s, 3H); 13C NMR (100 MHz, CDCl$_3$) δ 170.4, 168.6, 168.5, 155.3, 152.6, 152.2, 149.5, 148.8, 148.7, 146.0, 146.0, 141.0, 140.3, 140.3, 134.6, 134.5, 132.9, 132.7, 132.7, 132.6, 130.1, 129.6, 127.1, 126.5, 125.1, 125.0, 119.5, 119.4, 118.1, 116.2, 116.2, 116.2, 116.0, 115.9, 113.9, 112.7, 112.6, 102.1, 102.1, 95.2, 95.0, 75.3, 75.3, 73.4, 72.7, 65.9, 61.3, 61.3, 60.4, 60.4, 59.4, 59.4, 58.4, 58.2, 58.0, 57.7, 53.8, 49.0, 48.1, 47.9, 47.7, 41.2, 41.1, 32.9, 32.9, 28.1, 27.7, 20.5, 20.4, 15.8, 15.8, 9.6; |

Reference Example 1
Processes and products at each process regarding the synthesis of ecteinascidin 743 from the compound 5-3 is shown in following synthetic process F.
Synthetic Process F
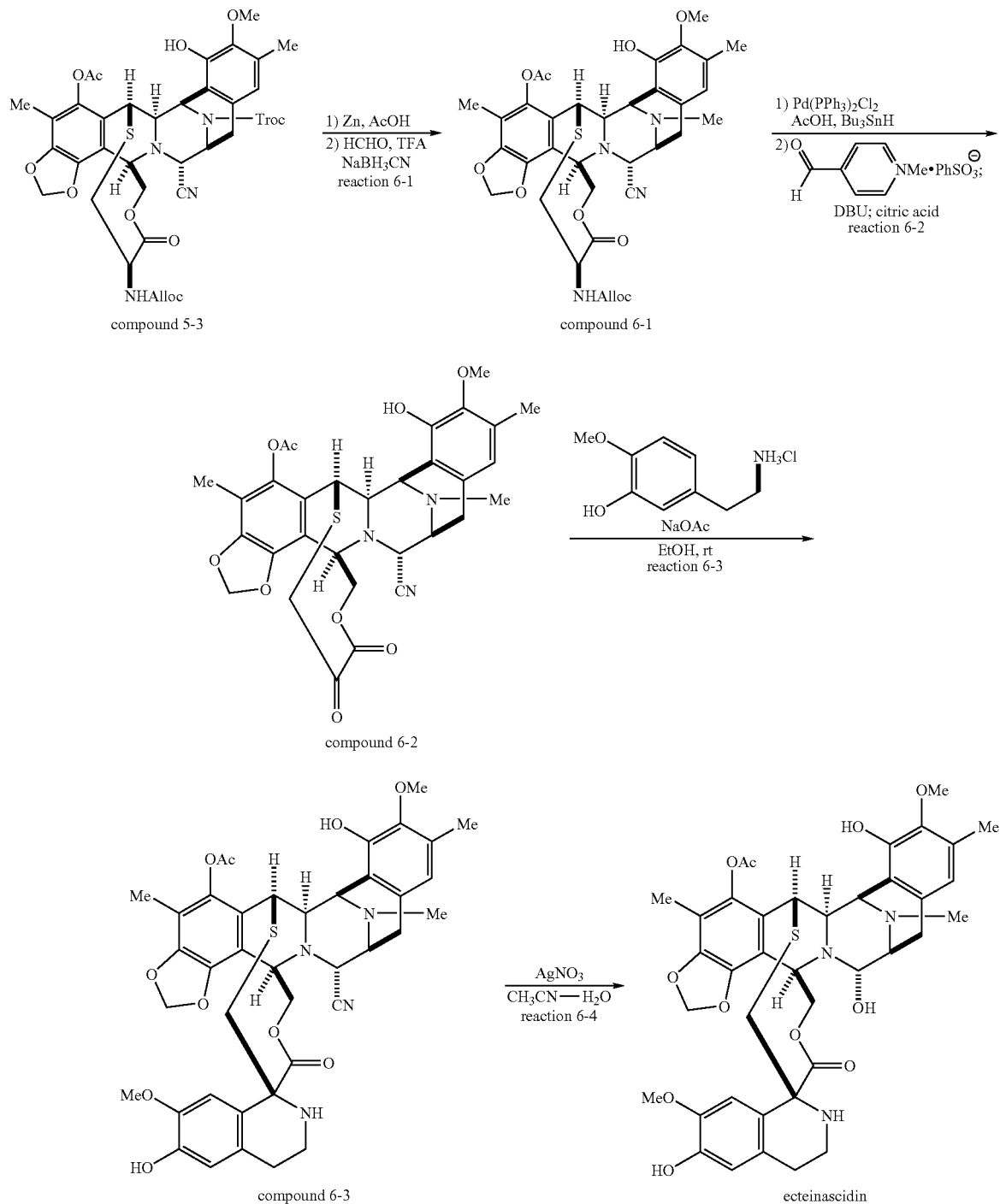

Detail of Synthesis of F

Synthesis of Compound 6-1

To the Et$_2$O (0.40 ml) solution of the compound 5-3 (17.3 mg, 0.0190 mmol) and zinc powder (96.1 mg, 1.47 mmol), AcOH (0.20 ml) was added at room temperature and stirred for 2.5 hours. Reaction solution was filtrate by Celite and concentrated by vacuum. EtOH was added to the residue and washed by saturated NaHCO$_3$ and brine. The organic layer was concentrated by vacuum and the residue was purified refined by PTLC (in 50% EtOAc n-hexane), thus amine (12.8 mg, 0.0175 mmol, 92%) was obtained as a colorless film. To amine (5.6 mg, 0.0076 mmol), aqueous solution (30 µl) of formalin and MeOH (0.4 ml) solution of NaBH$_3$CN (12 mg, 0.19 mmol); AcOH (0.10 ml) was added and stirred at room temperature for 1 hour. After concentrated by vacuum, the reaction solution was diluted by EtOAc and washed by saturated NaHCO$_3$ and brine. The organic layer was concentrated by vacuum, and the residue was purified by PTLC (in 50% EtOAct n-hexane), then the compound 6-1 (5.5 mg, 0.0074 mmol, 96%) was obtained as a colorless film. Physical properties of the Compound 6-1 are shown in Table 34.

Synthesis of Compound 6-2

To the CH$_2$Cl$_2$ (0.70 ml) solution of the compound 6-1 (8.6 mg, 0.012 mmol), Pd(PPh$_3$)Cl$_2$ (3.2 mg, 0.0045 mmol) and AcOH (15 µl, 0.26 mmol, 23 equivalent), n-Bu$_3$SnH (30 µl, 0.11 mmol) was added at room temperature for 20 minutes. The reaction solution was diluted by Et$_2$O, and after filtrated by Celite, concentrated by vacuum. The residue was refined by silica gel chromatography (in 10% MeOH CH$_2$Cl$_2$) and amine (6.4 mg, 0.010 mmol, 89%) was obtained as a white film.

To the mixed solvent of DMF (0.15 ml) and CH$_2$Cl$_2$ (0.15 ml) of amine (3.7 mg, 0.0059 mmol), 4-formyl-N-methylpyridine (16.5 mg, 0.057 mmol, 10 equivalent) was added and stirred at room temperature for 15 min. DBU (8.0 µl, 0.053 mmol) was added to the reaction solution and stirred at room temperature for 15 min. The reaction solution was diluted by CH$_2$Cl$_2$ (0.30 ml), then saturated citric acid aqueous solution (100 µl) was added and stirred for 40 minutes. Saturated NaHCO$_3$ aqueous solution and Et$_2$O were added, then Et$_2$O layer was concentrated by vacuum. The residue was purified by PTLC (in 70% EtOAc n-hexane), and the compound 6-2 (2.0 mg, 0.0032 mmol, 54%) was obtained as a white film Physical properties of the Compound 6-2 are shown in Table 35.

TABLE 34

| Compound 6-1 |
| --- |
| $[\alpha]_D^{23}$ −25.6° (c = 0.86, CHCl$_3$); IR (neat film) 3401, 1759, 1724, 1507, 1446, 1372, 1331, 1235, 1194, 1145, 1106, 1088, 1067, 998, 915 cm$^{-1}$; $^1$H NMR (400 MHz, CDCl$_3$) δ 6.78 (s, 1H), 6.08 (s, 1H), 6.08 (m, 1H), 5.99 (s, 1H9, 5.96 (m, 1H), 5.45 (d, J = 17.6 Hz, 1H), 5.31 (d, J = 17.6 Hz, 1H), 5.25 (d, J = 10.8 Hz, 2H), 5.02 (d, J = 12.0 Hz, 1H), 4.80 (m, 2H), 4.40-4.55 (m, 3H), 4.27-4.40 (m, 2H), 4.24 (s, 1H), 4.19 (m, 1H), 4.16 (m, 2H), 3.79 (s, 3H), 3.35-3.45 (m 2H), 2.85-2.97 (m, 2H), 2.29 (s, 3H), 2.27 (s, 3H), 2.20-2.40 (m, 1H), 2.20 (s, 3H), 2.13 (d, J = 16.4 Hz, 1H), 2.03 (s, 3H); $^{13}$C NMR (100 MHz, CDCl$_3$) δ 170.4, 168.6, 155.4, 150.8, 148.8, 145.7, 140.9, 140.3, 134.5, 132.8, 131.7, 129.9, 124.7, 124.6, 120.2, 118.0, 116.6, 113.5, 113.3, 102.0, 72.9, 65.8, 61.3, 60.4, 59.2, 59.1, 55.0, 54.5, 53.8, 41.6, 41.5, 32.8, 23.7, 20.4, 15.7, 9.6 |

TABLE 35

| Compound 6-2 |
| --- |
| $[\alpha]_D^{22}$ +153° (c = 0.20, CHCl$_3$); IR (neat film) 3447, 1763, 1723, 1622, 1589, 1500, 456, 373, 1270, 1236, 1194, 1160, 1145, 1108, 1087, 1063 cm$^{-1}$; $^1$H NMR (400 MHz, CDCl$_3$) δ 6.49 (s, 1H), 6.11 (s, 1H), 6.03 (s, 1H), 5.69 (s, 1H), 5.09 (d, J = 11.6 Hz, 1H), 4.66 (br, 1H), 4.39 (s, 1H), 4.24 (d, J = 4.8 Hz, 1H), 4.22 (d, J = 11.6 Hz,, 1H), 4.16 (d, J = 2.8 Hz, 1H), 3.76 (s, 3H), 3.54 (d, J = 4.8 Hz, 1H), 3.43 (dd, J = 9.6, 2.8 Hz, 1H), 2.90 (dd, J = 18.4, 9.6 Hz, 1H), 2.84 (d, J = 13.6 Hz, 1H), 2.70 (d, J = 18.4 Hz, 1H), 2.57 (d, J = 13.6 Hz, 1H), 2.33 (s, 3H9, 2.24 (s, 3H), 2.14 (s, 3H), 2.04 (s, 3H); $^{13}$C NMR (100 MHz, CDCl$_3$) δ 186.7, 168.5, 160.5, 147.1, 146.4, 142.9, 141.6, 140.7, 130.4, 129.8121.7, 121.7, 120.0, 117.9, 117.1, 113.5, 113.3, 102.2, 61.7, 61.4, 60.3, 59.8, 58.9, 54.6, 43.2, 41.6, 36.8, 24.1, 20.4, 15.8, 9.7 |

Synthesis of Compound 6-3

To the EtOH (0.25 ml) solution of the compound 6-2 (2.0 mg, 0.0026 mmol) and 3-hydroxy-4-methoxyphenylethylamine (12.4 mg, 0.062 mmol), NaOAc (7.4 mg, 0.090 mmol) was added at room temperature and stirred for 5.5 hours. After concentrated by vacuum, the residue was purified by PTLC (5% MeOH in $CH_2Cl_2$) and the compound 6-3 (2.4 mg, 0.0031 mmol, 96%) was obtained as a white film. Physical properties of the Compound 6-3 are shown in Table 36.

TABLE 36

Compound 6-3

$[\alpha]D^{23}$ −57.0° (c = 0.24, $CHCl_3$); IR (neat film) 3437, 2931, 1743, 1591, 1507, 1456, 1369, 1236, 1193, 1107, 1087, 1053, 1028 $cm^{-1}$; $^1H$ NMR (400 MHz, $CDCl_3$) δ 6.60 (s, 1H), 6.48 (s, 1H), 6.45 (s, 1H), 6.05 (s, 1H), 5.98 (s, 1H), 5.73 (s, 1H), 5.38 (br, 1H), 5.02 (d, J = 11.6 Hz, 1H), 4.57 (br, 1H), 4.33 (s, 1H), 4.28 (d, J = 5.2 Hz, 1H), 4.19 (d, J = 2.8 Hz, 1H), 4.12 (dd, J = 11.6, 2.8 Hz, 1H), 3.79 (s, 3H), 3.63 (s, 3H), 3.51 (d, J = 4.8 Hz, 1H), 3.42 (m, 1H), 3.10 (ddd, J = 11.6, 10.8, 4.0 Hz, 1H), 2.94 (m, 2H), 2.78 (m, 1H), 2.62 (m, q1H), 2.47 (m, 1H), 2.35 (m, 1H), 2.32 (s, 3H), 2.27 (s, 3H), 2.20 (s, 3H), 2.09 (m, 1H), 2.04 (s, 3H); $^{13}C$ NMR (100 MHz, $CDCl_3$) δ 172.6, 168.1, 147.8, 145.3, 144.5, 144.3, 143.0, 141.3, 140.1, 130.8, 129.3, 129.1, 125.8, 121.2, 120.7, 118.2, 118.1, 114.1, 114.1, 113.4, 109.8, 101.9, 64.6, 61.1, 60.4, 60.0, 59.7, 59.5, 55.2, 54.7, 54.6, 42.2, 41.8, 41.6, 39.6, 28.8, 24.2, 20.5, 15.8, 9.7;

Synthesis of Compound 6-4

To the $CH_2CN$ (0.3 ml) and $H_2O$ (0.2 ml) mixed solution of the compound 6-3 (2.4 mg, 0.031 mmol, 1.0 equivalent), $AgNO_3$ (10.2 mg, 0.060 mmol) was added and stirred at room temperature for 17 hours. EtOAc was added to the reaction solution, washed by saturated $NaHCO_3$ aqueous solution and the organic layer was dried by $Na_2SO_4$. Then concentrated by vacuum, and the compound 6-4 was obtained as a yellow film. Physical properties of the Compound 6-4 are shown in Table 37.

TABLE 37

Compound 6-4

$[\alpha]_D^{22}$ −58.0° (c=0.15, $CH_2Cl_2$); IR (neat film) 3347, 2930, 1763, 1741, 1590, 1509, 1458, 1431, 1369, 1237, 1195, 1122, 1109, 1088, 1053, 1029, 1003, 958, 916 $cm^{-1}$; $^1H$ NMR (400 MHz,) δ 6.61 (s, 1H), 6.47 (s, 1H), 6.45 (s, 1H), 6.02 (s, 1H), 5.94 (s, 1H), 5.69 8br, 1H), 5.39 (br, 1H), 5.13 (d, J=11.2Hz, 1H), 4.81 (s, 1H), 4.48 (d, J=3.3Hz, 1H), 4.48 (br, 1H), 4.16 (d, J=5.1Hz, 1H), 4.05 (dd, J=11.2Hz, 1H), 3.79 (s, 3H), 3.62 (s, 3H), 3.57 8d, J=4.9Hz, 1H), 3.22 (br, 1H), 3.12 (ddd, J=10.0, 10.0, 4.0Hz, 1H), 2.82-2.97 (m, 2H), 2.81 (m, 1H), 2.60 (ddd, J=15.9, 10.0, 4.0Hz, 1H), 2.48 (ddd, J=15.9, 4.0, 3.4Hz, 1H), 2.37 (br, 1H), 2.32 (s, 3H), 2.27 (s, 3H), 2.20 (s, 3H), 2.19 (br, 1H), 2.03 (s, 3H); $^{13}C$ NMR (100 MHz, $CDCl_3$) δ 172.6, 168.3, 147.7, 145.1, 144.4, 144.2, 142.9, 141.3, 140.5, 131.5, 129.2, 129.1, 121.8, 120.9, 117.9, 115.9, 114.0, 112.5, 109.8, 101.7, 82.1, 64.7, 61.3, 60.4, 57.8, 57.7, 56.0, 55.1, 54.9, 42.2, 42.1, 41.4, 39.7, 28.9, 24.1, 20.5, 15.8, 9.7;

| Illustration list of abbreviations | |
|---|---|
| MOMO: | methoxymethoxy |
| TFA: | trifluoroacetic acid |
| TF : | trifluoromethansulfonyl |
| Silyl groups | |
| TIPS: | tri isopropylsilyl group |
| TBS: | t-butyldimethyl silyl group |

| -continued | |
|---|---|
| Illustration list of abbreviations | |
| TBDPS: | t-butyl diphenyl silyl group |
| TES: | triethylsilyl group |
| TMS: | trimethylsilyl group |
| Dppf: | diphenyl phosphiferrocene |
| Ts | p-toluenesulfonyl |
| CSA : | camphor sulfonic acid |
| Bn : | benzyl |
| TMG: | N,N,N,N-tetramethylguanidine |
| PMP: | paramethoxyphenyl |
| TABF: | tetrabutylammonium florid |
| DMAP: | dimethylaminopyridine |
| Ms: | methansulfonyl |
| TEM: | triethylamine |
| Boc: | tertiary buthoxycarbonyl |
| Dba: | trans,trans-dibenzylidene acetone |
| Troc: | trichloroethoxycarbonyl |
| $G/GHNO_3$: | guanidineaqueous solution |
| Red-Al: | $[(MeOCH_2CH_2)_2AlH_2]Na$ |
| Alloc: | allyloxycarbonyl |
| WSCDD•HCl: | 1-(dimethylaminopropy1)-3-ethylcarbodiimide hydrochloric acid salt |
| DBU: | diazabicyclo[5,4,0]undecene-7-en |

INDUSTRIAL APPLICABILITY

As mentioned above, by utilizing the intermediates and reaction processes of the present invention, various intermediates and analogues of Et743 can be provided, further excellent effect that these compounds can be effectively produced is provided.

The invention claimed is:

1. An amine compound represented by formula 4,

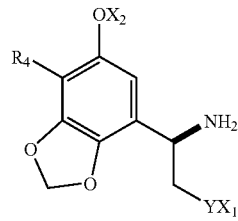

formula 4 wherein, $R_4$ is H or an alkyl group of carbon number 4 or less, $X_2$ is selected from the group consisting of H or an alkyl group of carbon number 4 or less, an alkoxyalkyl group, an allyl group, or an alkyl or arylsulfonyl group, Y is oxygen or NH, and $X_1$ is a hydrogen, protecting group of amino group or a silyl groups consisting of an acyl group of carbon number 4 or less, t-butyldiphenylsilyl (TBDPS), triisopropylsilyl (TIPS), t-butyldimethylsilyl (TBS), triethylsilyl (TES), and trimethylsilyl (TMS), by Ugi reaction.

2. The amine compound of claim 1, wherein Y is oxygen, $X_1$ is selected from silyl groups consisting of an acyl group of carbon number 4 or less, t-butyldiphenylsilyl (TBDPS), triisopropylsilyl (TIPS), t-butyldimethylsilyl (TBS), triethylsilyl (TES), and trimethylsilyl (TMS).

3. The amine compound of claim 2, produced by the processes displayed by reactions 2-1, 2-2, 2-3, 2-4, 2-5, 2-6, 2-7 and 2-8,

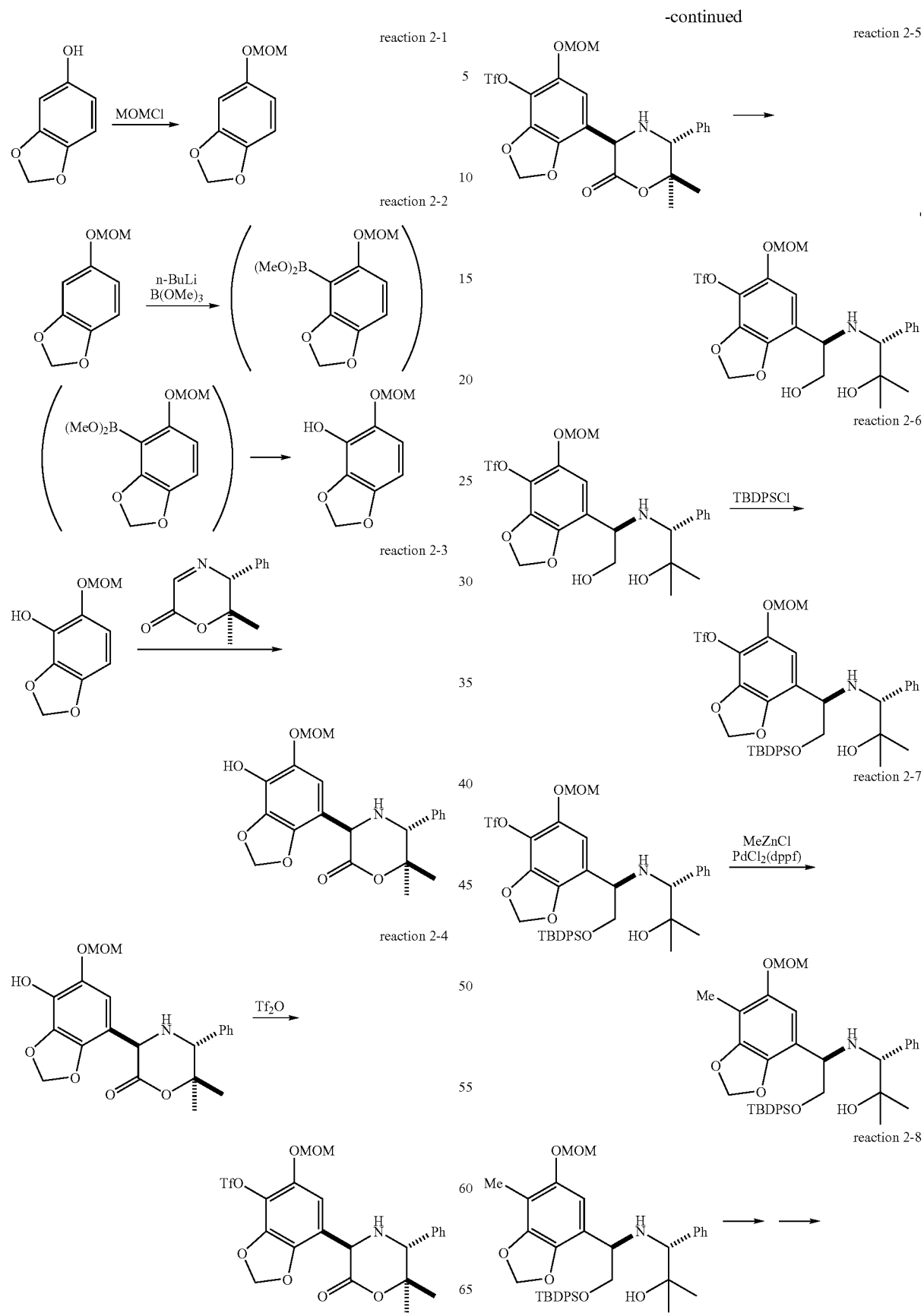

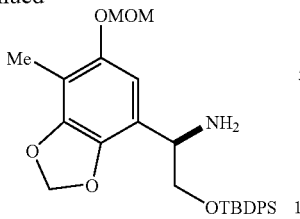

wherein the reaction 2-1 is a transforming reaction from a $C_5$ hydroxyl group to a methoxymethyl group (MOM), the reaction 2-2 is an introducing reaction of hydroxyl group to $C_{22}$, the reaction 2-3 is a Mannich reaction, the reaction 2-4 is a transforming reaction of $C_6$ hydroxyl group to a trifluoromethanesulfonyl (TfO) group, the reaction 2-5 is a reducing reaction of lactone, reaction 2-6 is a transforming reaction of $C_{22}$ hydroxyl to t-butyldiphenylsilyl (TBDPS) group, reaction 2-7 is a methylation reaction of the $C_6$ TfO group and the reaction 2-8 is a transforming reaction to amine, wherein Y is oxygen, $X_1$ is t butyloxyphenylsilyl (TBOPS), $X_2$ is MOM, and $R_4$ is methyl (Me).

* * * * *